USOO5977061A

United States Patent [19]
Holy et al.

[11] Patent Number: 5,977,061
[45] Date of Patent: Nov. 2, 1999

[54] N⁶- SUBSTITUTED NUCLEOTIDE ANALAGUES AND THEIR USE

[75] Inventors: Antonin Holy, Horni Pocernice, Czech Rep.; Erik Desire Alice De Clercq, Lovenjoel, Belgium

[73] Assignees: Institute of Organic Chemistry and Biochemistry of the Academy of Sciences of the Czech Republic, Czech Rep.; Rega Stichting, v.z.w., Belgium

[21] Appl. No.: 08/426,372

[22] Filed: Apr. 21, 1995

[51] Int. Cl.⁶ .......................... A61K 31/675; A61K 38/02; C07F 9/38; C07K 2/00

[52] U.S. Cl. ................................. 514/7; 514/81; 530/345; 530/352; 530/409; 544/244; 546/23

[58] Field of Search .................................... 530/345, 352, 530/409; 514/7, 81; 544/244; 546/23

[56] References Cited

U.S. PATENT DOCUMENTS

| | | | |
|---|---|---|---|
| 4,659,825 | 4/1987 | Holy et al. | 544/244 |
| 4,724,233 | 2/1988 | De Clercq et al. | 514/81 |
| 4,808,716 | 2/1989 | Holy et al. | 544/244 |
| 5,142,051 | 8/1992 | Holy et al. | 544/243 |
| 5,208,221 | 5/1993 | Kim et al. | 514/81 |
| 5,302,585 | 4/1994 | Yu et al. | 514/81 |
| 5,352,786 | 10/1994 | Jindrich et al. | 544/243 |
| 5,356,866 | 10/1994 | Arai et al. | 504/292 |
| 5,356,886 | 10/1994 | Harnden | 514/81 |
| 5,514,798 | 5/1996 | Bischofberger et al. | 544/243 |
| 5,591,851 | 1/1997 | Alexander | 544/243 |

FOREIGN PATENT DOCUMENTS

| | | | |
|---|---|---|---|
| 0 269 947 B1 | 6/1988 | European Pat. Off. | C07F 9/547 |
| 0 398 231 A2 | 11/1990 | European Pat. Off. | C07H 19/10 |
| 0 421 819 A1 | 4/1991 | European Pat. Off. | |
| 0 434 450 A2 | 6/1991 | European Pat. Off. | |
| 0 454 427 A1 | 10/1991 | European Pat. Off. | |
| 0 468 119 A1 | 1/1992 | European Pat. Off. | C07F 9/6561 |
| 0 481 214 A1 | 4/1992 | European Pat. Off. | C07F 9/6561 |
| 618214 | 10/1994 | European Pat. Off. | |
| 0 369 409 B1 | 1/1995 | European Pat. Off. | |
| WO 93/07157 | 4/1993 | WIPO. | |
| WO 94/03467 | 2/1994 | WIPO. | |
| WO 95/07920 | 3/1995 | WIPO. | |

OTHER PUBLICATIONS

Ching et al., "Nonclinical toxicology and in vitro Toxicity Studies with the Novel Anti–HIV Agent (1S,4R)–4–[2–Amino–6–(Cyclopropylamino)–9H–Purin–9–YL]–2–Cyclopentene–1–Methanol (1592U89) Succinate," Presentations @ the 34th Interscience Conf. on Antimicrobial Agents & Chemotherapy, Orlando, Florida Abstract # 188 (Oct. 4–7, 1994).

Cihlar et al., "Transport of 9–(2–Phosphonomethoxyethyl)Adenine across Plasma Membrane of HeLa S3 Cells Is Protein Mediated," Antimicro AG & Chemo 39(1):117–124 (1995).

Colla, et al., "Synthesis of aliphatic nucleoside analogues with potential antiviral activity," Eur J Med Chem 17:569–576 (1982).

Daluge et al., "1592U89 Succinate—A Novel Carbocylic Nucleoside Analog With Potent, Selective Anti–HIV Activity," Presentations @ the 34th Interscience Conf. on Antimicrobial Agents & Chemotherapy, Orlando, Florida Abstract # 16 (Oct. 4–7, 1994).

De Clercq et al., "Antiviral activity of phosphonylmethoxyalkyl derivatives of purine and pyrimidines," Antiviral Res 8:261–272 (1987).

Faletto et al., "Unique Intracellular Activation of a New Anti–HIV Agent (1S,4R)–4–[2–Amino–6–(Cyclopropylamino)–9H–Purin–9–YL]–2–Cyclopentene–1–Methanol (1592U89) in the Human T–Lymphoblastoid Cell Line CEM–T4," Presentations @ the 34th Interscience Conf. on Antimicrobial Agents & Chemotherapy, Orlando, Florida Abstract # 184 (Oct. 4–7, 1994).

Good et al., "Disposition in Monkeys and Mice of (1S, R4)–4–[2–Amino–6–(Cyclopropylamino)–9H–Purin–9–YL)–2– Cyclopentene–1–Methanol (1592U89) Succinate, A Potent Inhibitor of HIV," Presentations @ the 34th Interscience Conf. on Antimicrobial Agents & Chemotherapy, Orlando, Florida Abstract # 186 (Oct. 4–7, 1994).

Holy et al., "Antiviral Acyclic Nucleotide Analogues," Antibiotics and Antiviral Compounds 455–462 (1993).

Schaeffer, et al, "Enzyme Inhibitors. VIII. Studies on the Mode of Binding of Some 6–Substituted 9–(Hydroxyalkyl)purines to Adenosine Deaminase," J Med Chem 8(4):502–506 (1965).

Tisdale et al., "Anti–HIV Activity of (1S,4R)–4–[2–Amino–6–(Cyclopropylamino)–9H–Purin–9–YL]–2Cyclopentene–1–Methanol (1592U89)," Presentations @ the 34th Interscience Conf. on Antimicrobial Agents & Chemotherapy, Orlando, Florida Abstract # 182 (Oct. 4–7, 1994).

Balzarini et al., "Differential Antiherpesvirus and Antiretrovirus Effects of the (S) and (R) Enantiomers of Acyclic Nucleoside Phosphonates: Potent and Selective In Vitro and In Vivo Antiretrovirus Activities of (R)–9–(2–Phosphonomethoxypropyl)–2,6–Diaminopurine," Antimicrobial Agents and Chemotherapy, 37(2):332–338 (1993).

Dvorakova et al., "Synthesis and Antiviral Activity of Acyclic Nucleoside and Nucleotide Derivatives of 8–Azaadenine," Collect. Czech. Chem. Commun., 58:253–255 (1993).

(List continued on next page.)

*Primary Examiner*—Jeffrey E. Russel
*Attorney, Agent, or Firm*—Max D. Hensley

[57] ABSTRACT

Novel PMP, PME and HPMP and related compounds containing N-6 substituted 2,6-diaminopurine and adenine bases are provided. These compounds are useful in a variety of utilities, including as intermediates in the preparation of flame retardants, diagnostic reagents and therapeutics, including antivirals. Of particular note are compounds otherwise not known to possess anti-DNA viral activity that become potent inhibitors of DNA viruses upon substitution of the N-6 site, thereby providing a novel and unexpected and surprising use for such compounds.

33 Claims, No Drawings

OTHER PUBLICATIONS

Dvorakova et al., "Synthesis and Biological Effects of 9–(3–Hydroxy–2–Phosphonomethoxypropyl)Derivatives of Deazapurine Bases," Collect. Czech. Chem. Commun., 58:1403–1418 (1993).

Holy et al., "Phosphonylmethyl Ethers of Nucleosides and Their Acyclic Analogues," Am. Chem. Soc., Nucleotide Analogues, Chpt. 4, pp. 51–71 (1989).

Naesens et al., "HPMPC (Cidofovir), PMEA (adefovir) and Related Acyclic Nucleoside Phosphonate Analogues: A Review of their Pharmacology and Clinical Potential in the Treatment of Viral Infections," Antiviral Chem. & Chemotherapy, 8(1):1–23 (1997).

N⁶-SUBSTITUTED NUCLEOTIDE ANALAGUES AND THEIR USE

This application relates to nucleotide analogues and to their use in suitable utilities, especially diagnostic and therapeutic methods. It also relates to the use of such nucleotide analogues as haptenic labels.

Nucleotide analogues containing phosphonate groups are disclosed for example in U.S. Pat. Nos. 4,659,825, 4,808,716, 4,724,233, 5,142,051, 5,302,585, 5,208,221, 5,352,786, 5,356,886, in EP publication numbers 269,947, 481,214, 630,381, 369,409, 454,427, 618,214 and 398,231 and in WO 95/07920 and WO 94/03467. The teachings of these patents include compounds in which a phosphonate group is linked to a defined purine base, generally at the 9-position of the base, by a 2-(methoxy)propyl group, a 2-(methoxy)ethyl group, a 2-methoxy-3-hydroxypropyl group, or a 2-methoxy-3-fluoropropyl group, known respectively as PMP, PME, HPMP and FPMP compounds. The purine bases may include the aza and deaza analogues thereof. Typical purine bases are adenine, 2,6-diaminopurine and guanine.

U.S. Pat. No. 5,142,051 discloses an (RS) HPMP compound in which the purine base is N⁶-dimethyladenin-9-yl.

EP 454,427 includes disclosure in which the purine bases of FPMP compounds are substituted by substituted amino (alkylamino disclosed).

EP 468,119 describes certain methoxyphosphonyl antiviral agents in which a purine heterocyclic base is substituted at the 6 position with "NHR" and at the 2 position with H or NH₂, but R is undefined.

EP 481,214 discloses certain methoxyphosphonyl antiviral compounds as antiviral agents for RNA or DNA viruses where the purine base is independently substituted at its 2 or 6 position with NHR⁵ or N(R⁵)₂, wherein R⁵ is C1–C20 alkyl, aryl or aryl-alkyl which may be substituted or unsubstituted by substituents independently selected from the group consisting of hydroxy, oxygen, nitrogen or halogen.

WO 94/03467 discloses PMP compounds for use in treating retroviruses in which the heterocyclic base is a purine or its analogues in which the 2 and/or 6 and/or 8 position is substituted by, among other things, alkylamino, aralkylamino, dialkylamino, heteroalkylamino, alkyloxyamino or heterocyclic amino, wherein alkyl is straight or branched chain saturated hydrocarbyl group containing C₁–C₆, such as methyl, ethyl, 2-propyl, n-pentyl or neopentyl; alkyloxy is O-alkyl; aralkyl or heteroaralkyl is —R—Ar where —R— is the alkylene counterpart of alkyl (—R) and Ar is a substituted (with hydroxyl, halo, amino, sulfonyl, carbonyl or C₁–C₃ alkyl substituted with hydroxyl, halo, amino, sulfonyl, or carbonyl) or an unsubstituted aromatic group having 6–10C and optionally a heteroatom selected from oxygen or nitrogen, e.g., phenyl, naphthyl, quinolyl or benzyl; aralkylamino and heteroaralkylamino are defined as groups of the formula —N(Z)2 wherein Z is independently H or —R—Ar (but at least 1 Z is —R—Ar); heterocyclic amino is a saturated or unsaturated heterocyclic ring containing at least 1 N atom (ordinarily 1) and optionally in addition at least 1 other heteroatom (examples being pyrrolidine, morpholine or piperidine). WO 94/03467 discloses that cyclic structures contain from 3 to 6 ring atoms and are monocyclic, and in some embodiments the substituents of purine 6-amino groups are taken together with purine N¹ to form an N-heterocycle fused to the purinyl moiety, as in N¹-N⁶-ethenoadenine. WO94/03467 discloses a number of specific (R) N⁶-substituted PMPDAP compounds, including 9-(R)-(2-phosphonomethoxypropyl)-2-amino-6-cyclohexyl aminopurine and 9-(R)-(2-phosphonomethoxypropyl)-2-amino-6-cyclopropylaminopurine.

WO 95/07920 discloses various antiviral methoxyphosphonyl compounds having protected heterocyclic bases in which amino groups are mono substituted with C₁–C₂₀ alkyl, wherein alkyl includes straight chain, branched or cyclic residues, including methyl, ethyl, propyl, cyclopropyl, isopropyl, n-, sec-, iso-, and tert-butyl, cyclobutyl and "cyclic N—, S— or O— heterocarbonyl" (such as piperidinyl or morpholino).

It is an object of this invention to provide antiviral compounds having an improved selectivity index, i.e., that are less toxic yet more efficacious than nucleotide analogues known heretofore.

EP 434,450 discloses certain non-phosphonyl nucleoside analogues containing 2,6-diaminopurine wherein the 6 position of the 2,6-diaminopurinyl base is substituted with cyclopropylamino or N-cyclopropyl-N-methylamino. EP 421,819 discloses a similar nucleoside analogue in which the substitution is cyclopropylmethylamino. Daluge et al. (34th Interscience Conference on Antimicrobial Agents and Chemotherapy, Oct. 4–7, 1994) discloses carbovir derivatives in which the 6 position of the purine is substituted with cyclopropylamino, N-cyclopropyl-N-methylamino or N-aziridinyl.

Cihlar et al., "Antimicrobial Agents and Chemotherapy" 39(1):117–124 (1995) disclose N⁶-aminohexyl-PMEDAP.

It is an object to prepare compounds that are suitable as haptenic labels for oligonucleotide probes and polypeptides.

It is an additional object to provide compounds useful in the preparation of fire retardant resins.

It is a further object to obtain nucleotide analogues that are useful as anti-infective agents.

It is another object of this invention to provide compounds useful in the treatment of DNA viruses.

SUMMARY OF THE INVENTION

The objects of this invention are accomplished by a method comprising treating a subject infected or at risk of infection by a DNA virus with a therapeutically acceptable dose of a compound having structure (1)

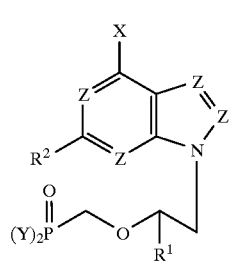

(1)

wherein

Y independently is OH, —OR³, —OCH(R¹⁶)OC(O)R³, a monophosphate, a diphosphate, an amino acid amidate, a polypeptide amidate, —NHR³, or —N(R³);

R³ independently is unsubstituted alkyl, aryl, alkenyl, alkynyl, alkaryl, alkynylaryl or alkenylaryl, and wherein H is substituted by halo, carboxy, hydroxyl, cyano, nitro, N-morpholino, or amino; and/or R³ wherein —CH₂— has been substituted by NH, S, or O;

R² is NH₂ or H;

R¹ is CH₃, C≡CH, CH=CH₂, CH₂F or azidomethyl;

R¹⁶ is H or R³; and

X is —N($R^{10}$)$_2$ wherein
$R^{10}$ independently is
  H,
  $C_1$–$C_{15}$ alkyl, $C_2$–$C_{15}$ alkenyl, $C_6$–$C_{15}$ arylalkenyl, $C_6$–$C_{15}$ arylalkenyl, $C_2$–$C_{15}$ alkynyl, $C_1$–$C_6$-alkylamino-$C_1$–$C_6$ alkyl, $C_5$–$C_{15}$ aralkyl, $C_6$–$C_{15}$ heteroaralkyl, $C_4$–$C_6$ aryl, $C_2$–$C_6$ heterocycloalkyl,
  $C_2$–$C_{15}$ alkyl, $C_3$–$C_{15}$ alkenyl, $C_6$–$C_{15}$ arylalkenyl, $C_3$–$C_{15}$ alkynyl, $C_7$–$C_{15}$ arylalkenyl, $C_1$–$C_6$-alkylamino-$C_1$–$C_6$ alkyl, $C_5$–$C_{15}$ aralkyl, $C_6$–$C_{15}$ heteroalkyl or $C_3$–$C_6$ heterocycloalkyl wherein methylene in the alkyl moiety not adjacent to NH has been replaced by —O—,
  optionally both $R^{10}$ are joined together to form a saturated or unsaturated $C_2$–$C_5$ heterocycle containing one or two N heteroatoms and optionally an additional O or S heteroatom,
  or one of the foregoing $R^{10}$ groups in which H is substituted with 1 to 3 halo, CN or $N_3$ but one or two $R^{10}$ groups are not H; and
Z is N or CH, provided that no more than one Z varies from purine; and the therapeutically acceptable salts thereof.

Unexpectedly and surprisingly, $N^6$ substitution of adenine or diaminopurine results in the acquisition of extremely high potency against DNA viruses on the part of the defined compounds. Such compounds otherwise have been considered to have little or no activity against DNA viruses.

Also provided in accordance with this invention are novel compounds having structure (2)

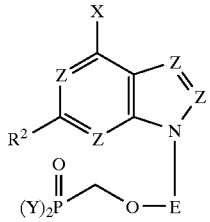

(2)

wherein
Y independently is, OH, —$OR^3$, —OCH($R^{16}$)OC(O)$R^3$, a monophosphate, a diphosphate, an amino acid amidate, a polypeptide amidate, —$NHR^3$, or —N($R^3$);
X is —N($R^{10}$)2;
Z is N or CH, provided that no more than one Z varies from purine;
$R^3$ independently is unsubstituted alkyl, aryl, alkenyl, alkynyl, alkaryl, alkynylaryl or alkenylaryl; $R^3$ wherein H is substituted by halo, carboxy, hydroxyl, cyano, nitro, N-morpholino, or amino; and/or $R^3$ wherein —$CH_2$— has been substituted by NH, S, or O;
$R^2$ is $NH_2$ or H;
E is —($CH_2$)$_2$—, —CH($CH_3$)$CH_2$—, —CH($CH_2$F)$CH_2$—, —CH($CH_2$OH)$CH_2$—, —CH(CH=$CH_2$)$CH_2$—, —CH(C≡CH)$CH_2$—, —CH($CH_2N_3$)$CH_2$—,

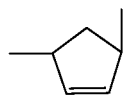

(3)

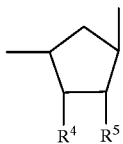

(4)

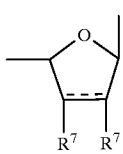

(5)

—CH($R^6$)OCH($R^{6'}$)—, —CH($R^9$)$CH_2$O— or —CH($R^8$)O—, wherein the right hand bond is linked to the 9 position of the purine, monoazapurine or monodeazapurine heterocycle and wherein Y and the hydroxyl group of —CH($CH_2$OH)$CH_2$—, $R^4$, $R^6$, $R^8$, or $R^9$ are joined to form a 6 membered ring;
the broken line represents an optional double bond;
$R^4$ and $R^5$ are independently hydrogen, hydroxy, halo, amino or a substituent having 1–5 carbon atoms selected from acyloxy, alkoxy, alkylthio, alkylamino and dialkylamino;
$R^6$ and $R^{6'}$ are independently H, $C_1$–$C_6$ alkyl, $C_1$–$C_6$ hydroxyalkyl, or $C_2$–$C_7$ alkanoyl;
$R^7$ are independently are H, $C_1$–$C_6$ alkyl, or are taken together to form —O— or —$CH_2$—;
$R^8$ is H, $C_1$–$C_6$ alkyl, $C_1$–$C_6$ hydroxyalkyl or $C_1$–$C_6$ haloalkyl;
$R^9$ is H, hydroxymethyl or acyloxymethyl; and
$R^{10}$ independently is
  H,
  $C_1$–$C_{15}$ alkyl, $C_2$–$C_{15}$ alkenyl, $C_6$–$C_{15}$ arylalkenyl, $C_6$–$C_{15}$ arylalkenyl, $C_2$–$C_{15}$ alkynyl, $C_1$–$C_6$-alkylamino-$C_1$–$C_6$ alkyl, $C_5$–$C_{15}$ aralkyl, $C_6$–$C_{15}$ heteroaralkyl, $C_4$–$C_6$ aryl, $C_2$–$C_6$ heterocycloalkyl,
  $C_2$–$C_{15}$ alkyl, $C_3$–$C_{15}$ alkenyl, $C_6$–$C_{15}$ arylalkenyl, $C_3$–$C_{15}$ alkynyl, $C_7$–$C_{15}$ arylalkenyl, $C_1$–$C_6$-alkylamino-$C_1$–$C_6$ alkyl, $C_5$–$C_{15}$ aralkyl, $C_6$–$C_{15}$ heteroalkyl or $C_3$–$C_6$ heterocycloalkyl wherein methylene in the alkyl moiety not adjacent to NH has been replaced by —O—,
  optionally both $R^{10}$ are joined together to form a saturated or unsaturated $C_2$–$C_5$ heterocycle containing one or two N heteroatoms and optionally an additional O or S heteroatom,
  or one of the foregoing $R^{10}$ groups in which H is substituted with 1 to 3 halo, CN or $N_3$ but one or two $R^{10}$ groups are not H;
$R^{16}$ is H or $R^3$; and
the therapeutically acceptable salts thereof;
provided, however, that
  (a) when E is —CH($CH_3$)$CH_2$— and $R^2$ is $NH_2$ then $R^{10}$ is not alkylamino, aralkylamino, pyrrolidino, piperidino or morpholino;
  (b) when E is —CH($CH_2$OH)$CH_2$— and $R^2$ is H, then $R^{10}$ is not dimethylamino, N-methyl-N-ethylamino or diethylamino; and
  (c) when E is —($CH_2$)$_2$— and $R^2$ is $NH_2$, then $R^{10}$ is not $C_5$–$C_7$ cycloalkyl.

DETAILED DESCRIPTION OF THE INVENTION

As used herein, and unless modified by the immediate context:

1. Alkyl means $C_1$–$C_{15}$ branched, normal or cyclic saturated hydrocarbons and includes methyl, ethyl, propyl, cyclopropyl, cyclobutyl, isopropyl, n-, sec-, iso- and tert-butyl, pentyl, isopentyl, 1-methylbutyl, 1-ethylpropyl, neopentyl, and t-pentyl.

2. Alkenyl means $C_2$–$C_{15}$ branched, normal or cyclic hydrocarbons containing at least 1 (generally 1–3) cis or trans oriented conjugated or unconjugated double bond, including allyl, ethenyl, propenyl, isopropenyl, 1-, 2- and 3-butenyl, 1- and 2-isobutenyl and the like.

3. Alkynyl means $C_2$–$C_{15}$ branched, normal, or cyclic hydrocarbon bearing at least 1 (generally 1–3) triple bond, e.g., 2-propynyl.

4. Aryl or heteroaryl means an resonant cyclic or fused polycyclic ring structure containing at least one 3–6 membered ring containing ring atoms solely of carbon or of carbon and one or two N—, S— or O— heteroatoms, including for example phenyl, 2- and 4-imidazolyl, 2-, 4- and 5-oxazolyl, 2-, 3-, 4- or 5-isoxazolyl, 2-, 3-, 4- or 5-furazanyl, 2-, 4- and 5-thiazolyl, 3-, 4-, 5-isothiazolyl, 3- and 4-pyrazolyl, 2-, 3- and 4-pyridinyl or 2-, 4- and 5-pyrimidinyl, 1-, 2-, 3- or 4- azetidine, 2-, 3-, 4-, or 5-thiophene, 2-, 3-, 4-furanyl, 1-, 2-, 3-, 4-, or 5-pyrrolyl and analogues thereof in which a double bond has been shifted, e.g. 2H—pyrrole, or has been saturated, e.g. 2-pyrrolinyl or 3-pyrazolinyl. In general, while the foregoing are examples, any ring atom other than oxygen or nitrogen serves as the binding site for the N-6 amino group, although a ring nitrogen also is directly bonded to the 6-carbon of the purine in circumstances when two $R^{10}$ are taken together.

5. Arylalkenyl and aralkenyl respectively means alkynyl or alkenyl substituted with at least 1 (generally 1–3) aryl groups. When this is an $R^{10}$ group it is bonded through an aliphatic (saturated or unsaturated) or aryl carbon to $N^6$.

6. Heterocycloalkyl means any fully saturated alkyl group forming a ring having $C_3$–$C_6$ in which 1 to 3 $CH_2$ groups have been substituted with NH, O or S. Ordinarily, only 1 or 2 methylene groups are substituted by a heteroatom. Heterocycloalkyl includes the saturated counterparts of the heteroaryl groups defined above, and includes for example piperazinyl, morpholino, aziridinyl, pyrrolidinyl, imidazolidinyl, pyrazolidinyl, piperidinyl, tetrahydrofuranyl. As in the case with the unsaturated heterocycles described above, any ring atom other than oxygen or nitrogen serves as the binding site for the N-6 amino group, although a ring nitrogen also is directly bonded to the 6-carbon of the purine in circumstances when two $R^{10}$ are taken together.

$R^1$ typically is $CH_3$.

$R^2$ generally is H where the compounds herein are to be employed for the treatment or prophylaxis of DNA virus infections, but compounds in which $R^2$ is $NH_2$ are satisfactory.

$R^3$ is not a critical functionality and may vary widely. $R^3$ for example includes $C_3$–$C_6$ aryl (including phenyl, 2- and 3-pyrrolyl, 2- and 3-thienyl, 2-and 4-imidazolyl, 2-, 4- and 5-oxazolyl, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl), $C_3$–$C_6$ aryl substituted with halo, alkyl $C_1$–$C_{12}$ alkoxy, CN, $NO_2$, OH, carboxy, carboxyester, thiol, thiolester, $C_1$–$C_{12}$ haloalkyl (1–6 halogen atoms), $C_2$–$C_{12}$ alkenyl or $C_2$–$C_{12}$ alkynyl [including 2-, 3- and 4-alkoxyphenyl ($C_1$–$C_{12}$ alkyl), 2-, 3- and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4-dimethylaminophenyl, 2-, 3- and 4-methylmercaptophenyl, 2-, 3- and 4-halophenyl (including 2-, 3- and 4-fluorophenyl and 2-, 3- and 4-chlorophenyl], 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4-difluorophenyl and 3,5-difluorophenyl), 2-, 3-and 4-haloalkylphenyl (1 to 5 halogen atoms, $C_1$–$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$–$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, —$C_6H_4$—C(O)—O alkyl $C_1$–$C_5$, ($C_1$–$C_4$ alkyl, including 2-, 3- and 4-ethylsalicylphenyl), 2-,3- and 4-acetylphenyl, 1,8-dihydroxynaphthyl (—O—$C_{10}H_6$—OH) and aryloxyethyl [$C_6$–$C_9$ aryl (including phenoxyethyl)], 2,2'-dihydroxybiphenyl, alkoxyethyl [$C_1$–$C_6$ alkyl including —$CH_2$—$CH_2$—O—$CH_3$ (2-methoxyethyl)], alkyl substituted by OH or by 1 to 3 halo atoms (including —$CH_3$, —$CH(CH_3)_2$, —$C(CH_3)_3$, —$CH_2CH_3$, —$(CH_2)_2CH_3$, —$(CH_2)_3CH_3$ —$(CH_2)_5CH_3$, —$CH_2CH_2F$, —$CH_2CH_2Cl$, —$CH_2CF_3$, and —$CH_2CCl_3$), 2-,

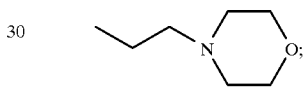

—N—2-N,N-dialkylaminophenyl, —$C_6H_4CH_2$—$N(CH_3)_2$, propylmorpholino, 2,3-dihydro-6-hydroxyindene, sesamol, catechol monoester, —$CH_2$—C(O)—$N(R^{11})_2$ wherein each $R^{11}$ is the same or different H or $C_1$–$C_4$ alkyl, —$CH_2$—S(O)($R^{11}$), —$CH_2$—$S(O)_2(R^{11})$, —$CH_2$—CH(OC(O)$CH_2R^{11}$)—$CH_2(OC(O)CH_2R^{11})$, cholesteryl, a 5 or 6 carbon monosaccharide, disaccharide or oligosaccharide (3 to 9 monosaccharide residues), enolpyruvate (HOOC—C(=$CH_2$)O), glycerol, α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids), trimethoxybenzyl, triethoxybenzyl, 2-alkylpyridinyl ($C_{1-4}$ alkyl),

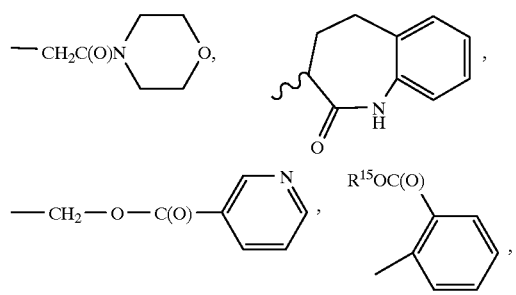

$C_1$–$C_4$ alkylene-$C_3$–$C_6$ aryl (including benzyl, —$CH_2$-pyrrolyl, —$CH_2$-thienyl, —$CH_2$-imidazolyl, —$CH_2$-oxazolyl, —$CH_2$-isoxazolyl, —$CH_2$-thiazolyl, —$CH_2$-isothiazolyl, —$CH_2$-pyrazolyl, —$CH_2$-pyridinyl and —$CH_2$-pyrimidinyl) substituted in the aryl moiety by 3 to 5 halogen atoms or 1 to 2 atoms or groups selected from halogen, $C_1$–$C_{12}$ alkoxy (including methoxy and ethoxy), cyano, nitro, OH, $C_1$–$C_{12}$ haloalkyl (1 to 6 halogen atoms; including —$CH_2$-$CCl_3$), $C_1$–$C_{12}$ alkyl (including methyl and ethyl), $C_2$–$C_{12}$ alkenyl or $C_2$–$C_{12}$ alkynyl, and other compounds set forth in Table 1a below. The hydroxyl groups of the compounds herein optionally are substituted with one of groups III, IV or V disclosed in WO94/21604.

$R^4$ and $R^5$ typically are H, halo or OH, preferably H.

$R^6$ and $R^{6'}$ generally are H or methyl. Usually, $R^6$ is H or methyl while $R^{6'}$ is H.

$R^7$ usually is H.

$R^8$ and $R^9$ typically are H, methyl or hydroxymethyl.

$R^{10}$ groups are an important functionality. They are responsible for the unexpected development of anti-DNA virus activity in the PMP series. One or both of these groups is other than H, but usually one is H.

Typically, the $R^{10}$ groups are relatively small, on the order of 1 to 6 carbon atoms and 1 to 3 N, S or O atoms in total for each $R^{10}$. When both $R^{10}$ are not hydrogen, one $R^{10}$ is optionally smaller than the other, e.g. one may contain 2–6 carbon atoms, and the other only 1.

Ordinarily the heteroatoms present in $R^{10}$ are not terminally located, i.e., they are substituted for $CH_2$ or CH. In some embodiments the heteroatom is donated by the 6-amino group, as occurs when two $R^{10}$ groups are cyclized to form a heterocyclic alkyl or aryl. In such cases, the N is bonded to the 6 carbon of the purine. However, it is not necessary that a heterocyclic alkyl or aryl that contains a ring N atom be bonded to C-6 via the N atom. It is also within the scope of this invention to bond such groups through ring carbon atoms directly or through intervening alkyl or alkoxyalkyl groups. Such intervening linking groups generally will be small ($C_1$–$C_4$), such as methylene, ethylene or ethoxy.

Ordinarily, $R^{10}$ is $C_1$–$C_6$ alkyl; $C_3$–$C_4$ cycloalkyl; $C_3$–$C_4$ cycloalkyl-substituted $C_1$–$C_2$ alkyl; $C_3$–$C_4$ cycloalkyl which is mono-, di- or tri-substituted with $C_1$–$C_3$ alkyl; —$CH(Phe)_2$; allyl; or allyl wherein H atoms are substituted with $C_1$–$C_3$ alkyl groups.

A particularly interesting embodiment is $R^{10}$ alkyl, alkylene or alkyne which further contains intrachain N and/or O atoms, wherein one intrachain N atom may be acidic or substituted with alkyl, typically $C_1$–$C_5$. Generally such $R^{10}$ groups will terminate in a single N(alk)$_2$ group wherein alk is alkyl as defined herein. Such $R^{10}$ groups usually are paired with an $R^{10}$=H or $C_1$–$C_4$ alkyl. Intrachain O or NH is used in any of the alkyl groups described herein, where the heteroatoms are used to substitute $CH_2$. Typical $R^{10}$ structures include —$(CH_2)_2N(CH_3)(CH_2CH_3)$, $(CH_2)_2N(CH_3)_2$, $(CH_2)_3N(CH_3)_2$ —$CH_2NHCH_2CH_2OCH_2NH(CH_3)_2$,—$CH_2NHCH_2OCH_2N(CH_3)_2$,

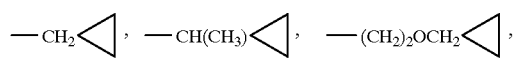

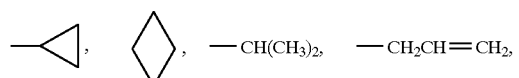

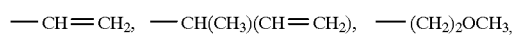

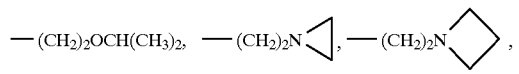

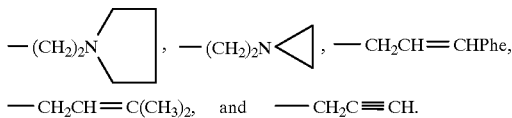

Instances in which two $R^{10}$ are joined together are

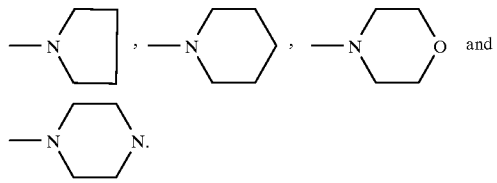

Hydrogen atoms of $R^{10}$ groups, particularly those described in the preceding two paragraphs, in turn are optionally substituted with halogen (especially F), cyano or azido. Typical embodiments include $CH_2F$, —$CH_2CN$, —$CH_2N_3$, —$CH_2$(fluorocyclopropyl), —$CHFCH_3$ or —$(CH_2)_2NH(CH_3)(CH_2F)$.

In some embodiments when $R^2$ is $NH_2$ then $R^{10}$ is $C_1$–$C_6$-alkylamino-$C_1$–$C_6$-alkylamino or pyrrolidino, but preferably the first.

$R^{10}$ groups may bear chiral N or C atoms. These are suitably used as the racemic or diastereomeric mixtures, or they may be chirally pure. In general, it is preferred that they be chirally pure.

Z usually is selected in order to produce a purine nucleus, although optionally it is chosen in order to yield an aza or deaza purine nucleus such as 1-deaza, 3-deaza, 8-aza or 7-deaza.

E generally is not an acetal (structure (5) or —CH($R^6$)OCH ($R^{6'}$)-). Typically, E is —$(CH_2)_2$—, —$CH(CH_3)CH_2$—, —$CH(CH_2OH)CH_2$—, —$CH(CH=CH_2)CH_2$—, —$CH(C\equiv CH)CH_2$—, —$CH(CH_2N_3)CH_2$—, —$CH(R^9)CH_2O$— or —$CH(R^8)O$—, most ordinarily, —$(CH_2)_2$—, —$CH(CH_3)CH_2$— or —$CH(CH_2OH)CH_2$—.

The chiral carbon atom(s) in the various E groups are diastereomers or racemates, or they optionally are enantiomerically pure or enriched. In general, one will select the enantiomers or diastereomers that have been found to be the most active in the parental compounds, e.g. the HPMP compound will be the (S) enantiomer, while the PMP compound will be the (R) enantiomer.

Group Y typically will be OH or convertible to OH by chemical or biological means. For in vivo hydrolysis Y usually is $OR^3$ in which $R^3$ is described above or Y is —$OCH(R^{16})OC(O)R^3$. Y is OPRT in intermediates for the most part. Certain end uses for intermediate compounds of the invention contemplate Y=an oligonucleotide or protein. PRT is a conventional hydroxyl protecting group.

Particularly useful Y groups are alkylacyloxymethyl groups and their derivatives, including —CH($CH_2CH_2OCH_3$)OC(O)C($CH_3$)$_3$,

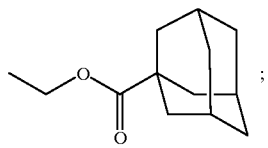

—$CH_2OC(O)C_{10}H_{15}$, —$CH_2OC(O)C(CH_3)_3$, —CH($CH_2OCH_3$)OC(O)C($CH_3$)$_3$, —CH(CH($CH_3$)$_2$)OC(O)C $(CH_3)_3$, $-CH_2OC(O)CH_2CH(CH_3)_2$, $-CH_2OC(O)C_6H_{11}$, $-CH_2OC(O)C6H_5$, $-CH_2OC(O)C_{10}H_{15}$, $-CH_2OC(O)CH_2CH_3$, $-CH_2OC(O)CH(CH_3)_2$, $-CH2OC(O)C(CH_3)_3$ and $-CH_2OC(O)CH_2C_6H_5$.

The use of amino protecting groups may be necessary during synthesis of the compounds of this invention, e.g. to protect the $R^2$ $NH_2$ group as required. In general, $R^{10}$ is not an amino protecting group that may have been used or would have been expected to be useful in known synthetic methods for the parental compounds herein. Amino protecting groups are described in Greene at pages 315–385 and include Carbamates (methyl and ethyl, 9-fluorenylmethyl, 9(2-sulfo) fluorenylmethyl 9-(2,7-dibromo)fluorenylmethyl, 2,7-di-t-butyl-[9-(10,10-dioxo-10,10,10,10-tetrahydrothioxanthyl)] methyl, 4-methoxyphenacyl); Substituted Ethyl (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chorobenzyl, 2,4-dichlorobenzyl, 4-methylsulfinylbenzyl, 9-anthrylmethyl, diphenylmethyl;) Groups With Assisted Cleavage such as 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl) benzyl, 5-benzisoxazolylmethyl, or 2-(trifluoromethyl)-6-chromonylmethyl; Groups Capable of Photolytic Cleavage, e.g., (m-nitrophenyl, 3,5-dimethoxybenzyl, o-nitrobenzyl, 3,4-dimethoxy-6-nitrobenzyl, phenyl(o-nitrophenyl) methyl); Urea-Type Derivatives (phenothiazinyl-(10)-carbonyl, N'-p-toluenesulfonylaminocarbonyl, N'-phenylaminothiocarbonyl); Miscellaneous Carbamates (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl); Amides (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl); Amides With Assisted Cleavage (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one); Cyclic Imide Derivatives (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3-5-triazacyclohexan-2-one, 1-substituted 3,5-dinitro-4-pyridonyl); N-Alkyl and N-Aryl Amines (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide), Imine Derivatives (N-1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene); Enamine Derivatives (N-(5,5-dimethyl-3-oxo-1-cyclohexenyl)); N-Metal Derivatives (N-borane derivatives, N-diphenylborinic acid derivatives, N-[phenyl(pentacarbonylchromium- or -tungsten)]carbenyl, N-copper or N-zinc chelate); N-N Derivatives (N-nitro, N-nitroso, N-oxide); N-P Derivatives (N-diphenylphosphinyl, N-dimethylthiophosphinyl, N-diphenylthiophosphinyl, N-dialkyl phosphoryl, N-dibenzyl phosphoryl, N-diphenyl phosphoryl); N-Si Derivatives; N-S Derivatives; N-Sulfenyl Derivatives (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-2,2,5,7,8-pentamethylchroman-6-sulfonyl, N-methanesulfonyl, N-β-trimethylsily ethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl), and especially carbamates and amides, still more typically, $-NHC(O)R^3$ or $-N=CR^4N(R^3)_2$.

In one embodiment of the compound of structure (1), $R^1$ is $CH_3$, Y is OH or $OR^3$, $R^2$ is H and X is $-N(CH_3)$ $(CH_2CH_3)$, $-N(CH_2CH_3)_2$, $-NHCH_2CH=CH_2$, $-NH$ $(CH_2)_2CH=CH_2$, $-NH(cyclopropyl)$, $-NH(CH_2)_2N$ $(CH_3)_2$, $-NH(CH_2)_3N(CH_3)_2$, $-NH(CH_2)_2N(CH_3)$ $(CH_2CH_3)$ $-NH(CH_2)_3N(CH_3)(CH_2CH_3)$, $-NH(CH_2)_2$ $NH(cyclopropyl)$, $-NH(CH_2)_3NH(cyclopropyl)$, $-NH$ $(CH_2)_2NHCH_2(cyclopropyl)$, $-NH(CH_2)_3NHCH_2$ $(cyclopropyl)$, $-NH(CH_2)_2NHCH_2CH=CH_2$, $-NH$ $(CH_2)_3$ $NHCH_2CH=CH_2$, $-NHCH_2C\equiv-CH$ or $-NHCH_2CH=CH(Phe)$.

UTILITIES

The novel compounds of this invention are useful per se or as intermediates in the preparation of polymers having a wide variety of diagnostic, therapeutic and industrial utilities.

The compounds are useful in the preparation of polyphosphonate flame retardants. The compounds of this invention that contain nonresonant sites of unsaturation, e.g., which contain vinyl, allyl or other sites of aliphatic unsaturation, are incorporated into polyvinyl polymers by methods heretofore employed to polymerize known vinylphosphonates, or methods clearly analogous thereto that will be apparent to the ordinary artisan. These monomers are copolymerized with vinyl resins by free radical catalysis methods already known per se, e.g., by use of persulfate or electron beam. The compounds of this invention that do not already contain vinyl groups are useful nonetheless as intermediates preparing vinylphosphonate monomers, or may be polymerized using other methods.

The compounds of this invention are also suitable as intermediates for use in the preparation of affinity absorption matrices that harness the chemical properties of the compounds' substituent groups. For example, the phosphonate groups in matrix bound form are useful in the chromatographic separation of positively charged molecules. Other immobilized examples of the compounds herein are useful in purifying proteins, e.g., enzymes involved in recognition of the compounds of this invention, e.g. transport proteins (see Cihiar, supra). Suitable methods of incorporation of the compounds of this invention into polymeric resins will be readily apparent to the skilled artisan, for instance the compounds are incorporated by cross-linking hydroxyl groups of the phosphonate or hydroxymethyl substituents using cross-linking agents heretofore known. Linking through a group other than the heterocyclic base will produce a resin useful in hydrophobic affinity chromatography. Other suitable linking methods are described in Cihlar (supra).

The compounds of this invention are useful as intermediates in preparing labeled oligonucleotide probes, e.g., where Y becomes an oligonucleotide. These oligonucleotides are directly useful in assays for target nucleic acid sequences. Typically, the phosphonate group of the compounds of this invention is covalently bonded to the terminus of an oligonucleotide having a predetermined sequence, although any hydroxyl group of the compounds of the invention is useful for this purpose. The structure or sequence of the oligonucleotide is not important except insofar as it is binding-competent for its complementary sequence. Many oligonucleotides having this property are well known, e.g. conventional phosphodiester or phosphorothioate oligonucleotides.

The compounds of this invention generally will be terminally incorporated into the oligonucleotide. If they contain a nonphosphonyl free hydroxyl group, they optionally are incorporated internally into the sequence of the oligonucleotide. Terminally incorporated diphosphoryl compounds of this invention which contain no free hydroxyl capable of participating in chain elongation also are useful in DNA sequencing in essentially the same manner as deoxyNTPs have been used in the past (see example 8 of U.S. Pat. No. 5,276,143). The nucleotide analogues of the invention (when diphosphorylated) are useful as chain terminators for dideoxynucleotide-type DNA sequencing protocols, provided that the nucleotide analogue lacks a free hydroxyl group suitable for polymerase mediated chain elongation. These compounds will not have R=hydroxymethyl and do not possess a cyclic structure incorporating the phosphorus atom (although compounds having such excluded structures can be intermediates). The nucleotide analogue is included in a kit with other reagents (such as Klenow polymerase or T4 polymerase, dNTPs, etc) needed for DNA sequencing (Otvos, et al, "Nucl. Acids Res." 15:1763–1777 (1987).

If the oligonucleotide-incorporated compound of this invention is binding-competent for its complementary sequence, i.e., if it is capable of base-pairing, then this nucleotide monomer will participate in hybridization. It is not necessary, however, that the incorporated nucleotide analogue of this invention base pair or otherwise participate in hybridization. If it is located at the terminus of the oligonucleotide it will be useful as an immunological recognition site, or haptenic recognition site, to facilitate detection of the oligonucleotide by an antibody capable of binding the compound of this invention.

The compounds of this invention also are useful as linkers or spacers in preparing affinity absorption matrices (as opposed to functioning as affinity moieties per se as noted above), immobilized enzymes for process control, or immunoassay reagents. The compounds herein contain a multiplicity of functional groups that are suitable as sites for cross-linking desired substances. For example, it is conventional to link affinity reagents such as hormones, peptides, antibodies, drugs, and the like to insoluble substrates. These insolubilized reagents are employed in known fashion to absorb binding partners for the affinity reagents from manufactured preparations, diagnostic samples and other impure mixtures. Similarly, immobilized enzymes are used to perform catalytic conversions with facile recovery of enzyme. Bifunctional compounds are commonly used to link analytes to detectable groups in preparing diagnostic reagents.

Many functional groups present in the compounds of this invention are suitable for use in cross-linking. For example, the phosphonic acid is used to form esters with alcohols or amides with amines. The R groups substituted with OH, azido (which is reduced to amino if desired before cross-linking) or vinyl are exemplary suitable sites. Similarly, the amino, halo, acyl and other reactive sites found on group B are suitable. Suitable protection of reactive groups will be used where necessary while assembling the cross-linked reagent. In general, the compounds here are used by linking them through phosphonic acid to the hydroxyl or amino groups of the linking partner in the same fashion as shown herein, and covalently bonded to the other binding partner through an R group. For example a first binding partner such as a steroid hormone is esterified to the phosphonic acid of this invention and then this conjugate is cross-linked through hydroxymethyl R to cyanogen bromide activated SEPHAROSE, whereby immobilized steroid is obtained. Other chemistries for conjugation are well known. See for example Maggio, "Enzyme-Immunoassay" (CRC, 1988, pp 71–135) and references cited therein.

The oligonucleotides of this invention are labeled with any conventional detectable label, e.g. a fluorescent moiety such as fluorescein, radioisotopes such as $C_{14}$ or $H_3$, stable free radicals, avidin, biotin and the like all of which previously have been used as labels for immunoassays or diagnostic probes. The label will be present on the oligonucleotide or on the residue of the nucleotide analogue of this invention. Suitable labeling methods are well known and are readily used with reactive groups such as hydroxyl, allyl and the like. A simple method is to label the compound of this invention with $H_3$ by proton exchange. The compounds also are biotinylated using conventional methods. See for instance U.S. Pat. No. 5,276,143 for analogous structures. However, the oligonucleotides of this invention also are useful directly in diagnostic probe assays without an exogenous detectable label. In one embodiment of this alternative, antibodies are raised against the compounds of this invention. Such antibodies (which in turn are labelled or used in a double antibody configuration) bind to the analogue of this invention and thereby are useful in detecting its presence as label for a protein or oligonucleotide.

The compounds of the invention are useful for treatment of microbial infections, for treatment of tumors or for other indications described below.

Microbial infections treatable by the compounds of this invention include viruses, parasites, yeasts and fungi, but it is believed that the compounds are most effective against viruses, which constitutes the preferred utility. Exemplary viral infections include infections caused by DNA or RNA viruses including herpesviruses (CMV, HSV 1, HSV 2, EBV, varicella zoster virus EVzV) (the novel compounds of structure (1) are exceptionally potent against this virus, and therefore will be useful in the treatment of shingles and chicken pox, ordinarily by topical application), bovid herpesvirus type 1, equid herpesvirus type 1, HHV-6), papillomaviruses (HPV types 1–55 includes carcinogenic HPV), flaviviruses (including African swine fever virus and Japanese encephalitis virus), togaviruses (including Venezuelan equine encephalomyelitis virus), influenza viruses (types A–C), retroviruses HIV-1, HIV-2, HTLV-I, HTVL-II, SIV, FeLV, FIV, MoMSV), adenoviruses (types 1–8), poxviruses (vaccinia virus), enteroviruses (polio virus types 1–3, hepatitis A virus), gastroenteritis viruses (Norwalk viruses, rotaviruses), hantaviruses (Hantaan virus), papovaviruses, rhinoviruses, parainfluenza virus types 1–4, rabies virus, restiratory synctial virus (RSV), hepatitis viruses A, B, C and E, and the like.

The antiviral activity of individual nucleotide analogues is determined by routine assay of antiviral (or other antimicrobial) activity using enzyme inhibition assays, tissue culture assays, animal model assays and the like as will be understood by those skilled in the art.

Protozoan parasite infections are treated using the compounds of the invention. The term protozoa includes those members of the subphyla Sarcomastigophora and Sporozoa of the phylum Protozoa. More particularly, the term protozoa as used herein includes genera of parasitic protozoa which are important to man because they either cause disease in man or in his domestic animals. These genera for the most part are classified in the superclass Mastighphora of the subphylum Sarcomastigophora and the class Telosporea of the subphylum Sporozoa in the classification according to Baker (1969). Illustrative genera of these parasitic protozoa include Histomonas, Pneumocystis, Trypanosoma, Giardia, Trichomonas, Eimeria, Isopora, Leishmania, Entamoeba, Toxoplasma and Plasmodium. Parasitic protozoans include *Plasmodium falciparum, Plasmodium berghei, Plasmodium malariae, Plasmodium vivax, Leishmania braziliensis, Leishmania donovani, Trypanosoma cruzi, Trypanosoma brucei, Trypanosoma rhodesiense, Pneumocystis carinii, Entamoeba histolytica, Trichomonas vaginalis* and the like (de Vries, E., et al, "Mol. Biochem. Parasitol" 47:43–50 (1991)) and trypanosomes (Kaminsky et al. "J. Parasitol." 80(6):1026–30 (1994). The compounds in which R is $CH_2OH$ and B is 3-deazaadenine are particularly interesting in the treatment of malarial parasites.

Nucleotide analogues of the invention are used to treat yeast or fungal infections caused by *Candida glabrata, Candida ropicalis, Candida albicans*, and other Candida species, Cryptococcus species including *Cryptococcus neoformans*, Blastomyces species including *Blastomyces dermatidis*, Torulopsis species including *Torulopsis glabrata*, Coccidioides species including *Coccidioides immitis*, Aspergillus species and the like.

The therapeutically useful compounds of this invention are useful in oral or sustained release forms. In these uses an ester or other group is removed in vivo, e.g., hydrolyzed or oxidized, so as to yield for example a free amino or hydroxyl group. Suitable protecting or precursor esters or amidates are selected based on the substrate specificity of esterases and/or carboxypeptidases expected to be found within cells where precursor hydrolysis is desired. To the extent that the specificity of these enzymes is unknown, one will screen a plurality of nucleotide analogues of this invention until the desired substrate specificity is found. This will be apparent from the appearance of free phosphonate or of antimicrobial activity. One generally selects compounds that are (i) not hydrolyzed or hydrolyzed comparatively slowly in the upper gut, (ii) gut and cell permeable and (iii) hydrolyzed in the cell cytoplasm and/or systemic circulation. Screens with cells from particular tissues are used to identify precursors that are released in organs susceptible to a target viral or microbial infection, e.g. in the case of liver, precursor drugs capable of hydrolysis in the liver. Other infections, e.g. CMV or HIV, optionally are treated with a precursor that is hydrolyzed at substantially the same rate and to substantially the same degree in all tissues. Assays known in the art are suitable for these purposes, including intestinal lumen stability, cell permeation, liver homogenate stability and plasma stability assays. These assays are used to determine the bioavailability characteristics of the precursors. However, even if the derivatives are not converted in vivo they remain useful as chemical intermediates.

The nucleotide analogues of the invention also can be (1) applied to tissue culture systems to eliminate or reduce viral spread or growth during the production of biopharmaceuticals or other products (such as proteins or vaccines), (2) used to eliminate or reduce viral spread or growth in clinical samples (such as blood), and (3) used to stop growth of tissue culture or bacterial cells (using toxic amounts of compound) while leaving the cells to carry on with protein production.

Pharmaceutical formulations. Compounds herein and their physiologically acceptable salts (hereafter collectively referred to as the active ingredients) are formulated for administration by any route appropriate to the condition to be treated. The compounds and formulations preferably will be sterile.

The active ingredients are placed into pharmaceutical formulations. The formulations, both for veterinary and for human use, comprise at least one active ingredient, as above defined, together with one or more acceptable carriers therefor and optionally other therapeutic ingredients. The carrier (s) must be "acceptable" in the sense of being compatible with the other ingredients of the formulation and not deleterious to the recipient.

The formulations conveniently are presented in unit dosage form and may be prepared by any of the methods well known in the art of pharmacy. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

For external infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), typically 0.2 to 15% w/w and most typically 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogues.

The oily phase of the emulsions of this invention may be constituted from known ingredients in a known manner. This phase may comprise an emulsifier alone, or a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Emulsion stabilizers suitable for use in the formulation of the present invention include Tween® 60, Span® 80, cetostearyl alcohol, benzyl alcohol, myristyl alcohol, glyceryl mono-stearate and sodium lauryl sulfate. Suitable oils or fats include straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate or 2-ethylhexyl palmitate. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is typically is present in such formulations in a concentration of 0.01 to 20% by weight.

Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered by rapid inhalation through the nasal passage from a container of the powder. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents such as pentamidine for treatment of pneumocystis pneumonia.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described. Preferred unit dosage formulations are those containing a daily dose or unit daily sub-dose, as herein above recited, or an appropriate fraction thereof, of an active ingredient.

The present invention further provides veterinary compositions comprising at least one active ingredient as above defined together with a veterinary carrier therefor. Veterinary carriers are materials for administering the composition and may be solid, liquid or gaseous materials which are otherwise inert or acceptable in the veterinary art and are compatible with the active ingredient. These veterinary compositions may be administered orally, parenterally or by any other desired route.

Compounds herein optionally are used in controlled release pharmaceutical formulations containing as active ingredient one or more active compounds in which the release of the active ingredient is controlled and regulated to allow less frequent dosing or to improve the pharmacokinetic or toxicity profile of a given compound. In general, the compounds are administered from controlled release systems such as the intravitreous implant of WO 92/14450 or U.S. Pat. No. 5,098,443, or the matrices of U.S. Pat. No. 4,740,365 or U.S. Pat. No. 5,141,752. Many others are known and are suitable for use herein.

Therapeutic Administration. Suitable routes for administration include oral, rectal, nasal, topical (including ocular, buccal and sublingual), vaginal and parenteral (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

For each of the above-indicated therapeutic indications the amount required of an active ingredient (as above defined) will depend upon a number of factors including the severity of the condition to be treated, the infectious agent, whether the use is prophylactic or to treat an acute infection, the site of infection or pathology (e.g. CMV retinitis is treated systemically or by intravitreous injection, or in the treatment of HHV-6 in multiple sclerosis patients, optionally by intrathecal administration) and other factors ultimately at the discretion of the attending physician or veterinarian. In general, however, a suitable dose for consideration by the clinician will be in the range of analogous methoxyphosphonates (see supra), taking into account differences in potency, generally 0.1 to 250 mg per kilogram bodyweight of recipient per dose (including active ingredient(s) in a range between 0.1 mg and 250 mg/Kg/dose in increments of 0.5 mg/Kg/dose such as 2.5 mg/Kg/dose, 3.0 mg/Kg/dose, 3.5 mg/Kg/dose, etc), typically in the range 0.5 to 50 mg per kilogram body weight per dose and most usually in the range 1 to 15 mg per kilogram body weight per dose. Unless otherwise indicated all weights of active ingredient are calculated as compounds wherein Y is not a polymer.

The desired dose is administered at appropriate intervals in unit dosage forms, usually with a relatively higher induction dose and lower, less frequent maintenance doses. The compounds also are used prophylactically, for example, by administration on about from 1 to 7 days before viral infection. HPV tumors or growths and herpes lesions often are treated topically, either by local injection or by topical gels, ointments or the like.

Internally cyclized compounds generally are expected to have a higher oral bioavailability than the corresponding uncyclized nucleotide analogue and/or exhibit reduced toxicity when compared with the same dose of the corresponding uncyclized nucleotide analogue. In addition, the $N^6$-substituted compounds per se possess lower toxicity and are more selective than the comparable guanine derivatives. Thus, doses will be adjusted accordingly.

The compounds of the invention optionally are employed in combination with other therapeutic agents for the treatment or prophylaxis of the infections or conditions indicated above. Examples of such further therapeutic agents include agents that are effective for the treatment or prophylaxis of viral, parasitic or bacterial infections or associated conditions or for treatment of tumors or related conditions. These include 3'-azido-3'-deoxythymidine (zidovudine, AZT), 2'-deoxy-3'-thiacytidine (3TC), 2',3'-dideoxy-2',3'-didehydroadenosine (D4A), 2',3'-dideoxy-2',3'-didehydrothymidine (D4T), carbovir (carbocyclic 2',3'-dideoxy-2',3'-didehydroguanosine), 3'-azido-2',3'-dideoxyuridine, 5-fluorothymidine, (E)-5-(2-bromovinyl)-2'-deoxyuridine (BVDU), 2-chloro-2'-deoxyadenosine, 2-deoxycoformycin, 5-fluorouracil, 5-fluorouridine, 5-fluoro-2'-deoxyuridine, 5-trifluoromethyl-2'-deoxyuridine, 6-azauridine, 5-fluoroorotic acid, methotrexate, triacetyluridine, 1-(2'-deoxy-2'-fluoro-1-β-D-arabinosyl)-5-iodocytidine (FIAC), tetrahydroimidazo(4,5,1-jk)-(1,4)-benzodiazepin-2(1H)-thione (TIBO), 2'-nor-cyclicGMP, 6-methoxypurine arabinoside (ara-M), 6-methoxypurine arabinoside 2'-O-valerate, cytosine arabinoside (ara-C), 2',3'-dideoxynucleosides such as 2',3'-dideoxycytidine (ddC), 2',3'-dideoxyadenosine (ddA) and 2',3'-dideoxyinosine (ddI), acyclic nucleosides such as acyclovir, penciclovir, famciclovir, ganciclovir, acyclic nucleotides such as HPMPC, PMEA, PMEG, PMPA, PMPDAP, FPMPA, HPMPA and HPMPDAP, (2R, 5R)-9-[tetrahydro-5-(phosphonomethoxy)-2-furanyl]adenine, (2R, 5R)-1-[tetrahydro-5-(phosphonomethoxy)-2-furanyl]thymine, other antivirals including ribavirin (adenine arabinoside), 2-thio-6-azauridine, tubercidin, aurintricarboxylic acid, 3-deazaneoplanocin, neoplanocin, rimantidine, adamantine, and foscarnet (trisodium phosphonoformate), antibacterial agents including bactericidal fluoroquinolones (ciprofloxacin, pefloxacin and the like), aminoglycoside bactericidal antibiotics (streptomycin, gentamicin, amicacin and the like), β-lactamase inhibitors (cephalosporins, penicillins and the like), other antibacterials including tetracycline, isoniazid, rifampicin, cefoperazone, claithromycin and azithromycin, antiparasite or antifungal agents including pentamidine (1,5-bis(4'-aminophenoxy)pentane), 9-deazainosine, sulfamethoxazole, sulfadiazine, quinapyramine, quinine, fluconazole, ketoconazole, itraconazole, Amphotericin B, 5-fluorocytosine, clotrimazole, hexadecylphosphocholine and nystatin, renal excretion inhibitors such as probenecid, nucleoside transport inhibitors such as dipyridamole, dilazep and nitrobenzylthioinosine, immunomodulators such as FK506, cyclosporin A, thymosin α-1, cytokines including TNF and TGF-β, interferons including IFN-α, IFN-β and IFN-γ, interleukins including interleukin 1, 2, 3, 4, 5, 6, 7, 8, 10, 12, 13, macrophage/granulocyte colony stimulating factors including GM-CSF, G-CSF, M-CSF, cytokine antagonists including anti-TNF antibodies, anti-interleukin antibodies, soluble interleukin receptors, protein kinase C inhibitors and, particularly in treatment of HIV, cotherapy with IFN-α, IL-2 or IL-12.

Immunogens and Antibodies. The compounds of this invention are used as immunogens to prepare antibodies capable of binding specifically to the compounds or their metabolic products. The immunogenic compositions are useful as intermediates in the preparation of antibodies for use in diagnostic or quality control assays for the compounds or their metabolic products. The antibodies are useful for measuring the presence, absence or amounts of the compounds by any convenient homogenous or heterogenous procedure such as fluorescence polarization immunoassay, fluorescence immunoassay (using fluorescent labels such as fluorescein and the like), radioimmunoassay, enzyme immunoassay (using enzyme indicators such as alkaline phosphatase, horseradish peroxidase, glucose oxidase, urease and the like) and nephelometric inhibition assay by described methods (WO 92/22639). Competitive-type assays usually require the antibody, and a tracer (such as a fluorescent or radio label) conjugated to the compound to be assayed. The antibodies directed against the compounds of this invention desirably will not cross-react with naturally-occurring nucleotides or nucleosides.

The immunogens of this invention contain the precursor or hydrolytic products in association with an immunogenic substance such as a protein or peptide. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides.

Methods for the manufacture of hapten immunogens are conventional per se, and are useful here, taking into account the functional groups that are available for cross-linking. The polypeptide immunogen (or a polypeptide that is desired to be made immunogenic by cross-linking to a compound of this invention) may be conjugated to a site on the heterocyclic base rather than to the phosphonate moiety. In general, the site will be a phosphonyl hydroxyl cross-linked by amidation or esterification of the phosphonate by the polypeptide itself or by a cross-linking functionality covalently bonded to the polypeptide, whereby Y is an immunogenic protein having more than 50 amino acid residues, usually less than 1000. The conjugates are prepared in conventional fashion. For example, N-hydroxysuccinimide, succinic anhydride or N,N-disubstituted carbodiimides are useful in preparing the conjugates of this invention. Animals typically are immunized against the immunogenic conjugates and monoclonal antibodies prepared in conventional fashion.

SYNTHETIC METHODS

The compounds herein are prepared by methods known per se. See for example WO 94/03467 and WO 95/07920, or Scheme 1 below (note that any OH-alkylation protecting group can be used in place of isopropyl). In general, the 6-chloropurine is first alkylated in DMF either in the presence of an equivalent amount of sodium hydride or cesium carbonate at 60–100 degrees C. The products are then isolated by silica chromatography and crystallized from ethyl acetate by slow addition of petroleum ether until crystalization occurs (the 2-amino-6-chloropurinyl PME/PMP compounds are crystalline, but the 6-chloropurinyl PME/PMP compounds are oils). The obtained 6-chloro compound is treated in ethanol solution with an excess (5 to 10 times) of the corresponding amine under reflux. The reaction is followed by TLC or HPLC analysis. The mixture is then evaporated, deionized on a cation exchanger column (DOWEX 50), washed with 20% aqueous methanol, and the compound freed by the use of 2.5% ammonia in 20% aqueous methanol. The eluate is evaporated and dried over phosphorus pentoxide, the residue treated with 10% (v/v) bromotrimethylsilane in acetonitrile (5 ml per mM of compound) in order to deprotect the hydroxyl groups. The mixture is allowed to stand overnight and worked up as described in WO 94/03467.

It is not essential to employ the phosphonyl protecting group where it is expected that the $N^6$ substituent may be labile to the TMS deprotection, e.g. where $R^{10}$ is an alkyl ether. In this case the free acid is used as the starting material for addition of the amine.

In the following scheme, halogen, OMS, O-nitrobenzylsulfonyl, or O-trifyl are optionally used in place of OTs.

part c and FIG. 23 (1990) or Mazur et al., "Tetrahedron Let." 40(20):3949 at scheme (1) and page 3955 (1984). For example, an oligonucleotide chain is synthesized on a matrix such as controlled pore glass in the 3'-5' or 5' to 3' direction, whereby the 3' or 5' ends, respectively of the oligonucleotide are bonded to the matrix and the oligonucleotide is protected except for the terminal 5' or 3' hydroxyl, respectively, of the last nucleotide. The protected o-chlorophenyl derivative of the structure 1 compound is prepared, analogous to the starting material shown in FIG. 23 of Uhlmann et al. This is covalently bonded to a terminal OH of the oligonucleotide using the Uhlmann et al. method.

Alternatively, the compound of this invention is converted to the intermediate that is analogous to compound 12 of Mazur et al. This analogue is added to the oligonucleotide using essentially the dinucleotide preparative chemistry shown on page 3955 of Mazur et al. The pyridinium salt of the compound of this invention (without free hydroxyl groups) is condensed with the free 5' or 3' end of the otherwise protected oligonucleotide in the same way Mazur et al. condense phosphonate 12 with a second nucleoside unit using DCC in dry pyridine in the presence of Dowex 50.

Scheme 1

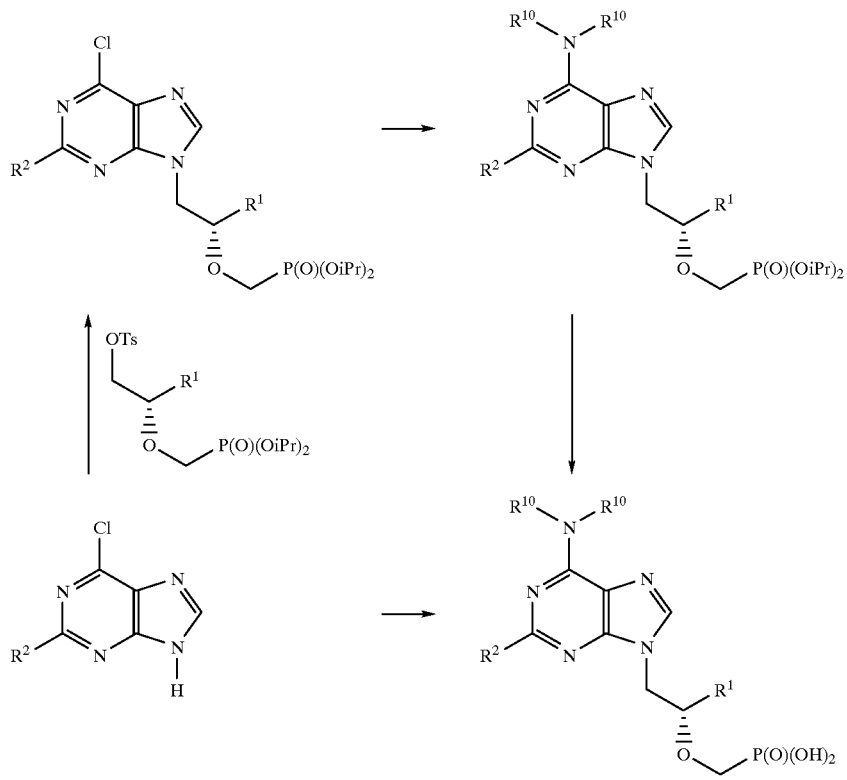

Phosphonylamidates, phosphonylesters and internally cyclized esters (where R=hydroxymethyl and a Y are taken together) are all prepared by methods analogous to those described in WO 95/07920 or other methods that will be apparent to the artisan.

Compounds of this invention where Y is an oligonucleotide are prepared from parental monomers in which Y is OH. The monomers are converted to the reactive intermediate using conventional chemistry, for example the method of Uhlmann et al., "Chemical Reviews" 90(4):543 at 553, After reaction by either method, the oligonucleotide is separated from the matrix (if present during the addition of the compound of this invention) and deprotected.

Alternatively, the compounds of this invention are chemically converted to nucleotide triphosphate analogues. This is accomplished using known reactions, for example reaction of the activated phosphonate (e.g. the morpholidate or imidazolidate with tris(tri-n-butylammonium) pyrophosphate in DMF.

Table 1a lists $R^3$ ester and Y amidate moieties that can be bonded via oxygen or directly, respectively, to the phosphorus atom. Esters of structures 1–5, 8–10 and 16, 17,19–22 are synthesized by reacting a nucleotide analogue having a free hydroxyl with the corresponding halide (chloride or acyl chloride and the like) and N,N-dicyclohexyl-N-morpholine carboxamidine (or another base such as DBU, triethylamine, $Cs_2CO_3$, N,N-dimethylaniline and the like) in DMF (or other solvent such as acetonitrile or N-methylpyrrolidone). Esters of structures 5–7, 11, 12, 21, and 23–26 are synthesized by reaction of the alcohol or alkoxide salt (or the corresponding amines in the case of compounds such as 13, 14 and 15) with the monochlorophosphonate or dichlorophosphonate or another activated phosphonate.

TABLE 1a

1. —$CH_2$—C(O)—$N(R^{15})_2$*
2. —$CH_2$—S(O)($R^{15}$)
3. —$CH_2$—$S(O)_2$($R^{15}$)
4. —$CH_2$—O—C(O)—$CH_2$—$C_6H_5$
5. 3-cholesteryl
6. 3-pyridyl
7. N-ethylmorpholino
8. —$CH_2$—O—C(O)—$C_6H_5$
9. —$CH_2$—O—C(O)—$CH_2CH_3$
10. —$CH_2$—O—C(O)—$C(CH_3)_3$
11. —$CH_2$—$CCl_3$
12. —$C_6H_5$
13. —NH—$CH_2$—C(O)O—$CH_2CH_3$
14. —$N(CH_3)$—$CH_2$—C(O)O—$CH_2CH_3$
15. —$NHR^3$
16. —$CH_2$—O—C(O)—$C_{10}H_{15}$
17. —$CH_2$—O—C(O)—$CH(CH_3)_2$
18. —$CH_2$—C#H(OC(O)$CH_2R^{15}$)—$CH_2$—(OC(O)$CH_2R^{15}$)*

19. —$CH_2$C(O)N⟨morpholine⟩

20. ⟨benzazepinone structure⟩

21. ⟨sugar ring with HO, OH, HO substituents⟩

22. —$CH_2$—O—C(O)—⟨3-pyridyl⟩

23. —$CH_2CH_2$—⟨2-pyridyl⟩

24. $CH_3$C(O)O—⟨o-methylphenyl⟩

TABLE 1a-continued

25. $CH_3CH_2$OC(O)—⟨o-methylphenyl⟩

26. —$CH_2$—⟨phenyl with $OCH_3$, $OCH_3$, $OCH_3$ substituents⟩

* — Each $R^{15}$ is the same or different $C_1$–$C_6$ alkyl (includes methyl, ethyl, propyl, isopropyl and t-butyl).
— chiral center is (R), (S) or racemate.

Other esters that are suitable for use herein are described in EP 632,048.

To the extent any compound of this invention cannot be produced by one of the foregoing methods other methods will be apparent to the artisan referring to conventional methods (see for instance Liotta et al. "Compendium of Organic Synthesis Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; March, J., "Advanced Organic Chemistry, Third Edition", (John Wiley & Sons, New York, 1985); as well as "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

EXAMPLES

Compounds were synthesized as described and assayed for activity against HSV-1, HSV-2, CMV, VZV, vaccinia virus, MSV, HIV-1 and HIV-2 using conventional methods in which inhibition of virus induced cytopathicity in either $E_6$SM or HEL cell cultures is assayed (see for example De Clercq et al. "J. Infect. Dis." 141:563 (1981) and "Nature" 323:464 (1986), Snoeck et al. "Antiviral Res." 21:197 (1993), Snoeck et al. "J. Med. Vir." 42:338 (1994) and Baba et al. "Eur. J. Clin. Microbiol." 6:158 (1987)). The following viruses were included in the study: herpes simplex virus type 1 (HSV-1), strain KOS and TK-deficient strains B 2006 and VMW 1837, HSV-2 (strain G), vaccinia virus (VV) and vesicular stomatitis virus (VSV) in $E_6$SM cells; cytomegalovirus strain AD-169 and strain Davis (HEL cells), varicella-zoster virus (VZV) strain OKA ($TK^+$), YS ($TK^+$), 07/1 ($TK^-$) and YS/R ($TK^-$) in HEL cells. The cell cultures were inoculated with 100 $CCID_{50}$, 1 h virus adsorption period.

The inhibition of HIV-induced cytopathicity in MT-4 or CEM/O cells was performed as described in Balzarini et al, "Proc. Natl. Acad. Sci. USA" 86:332 (1989). The cell cultures were inoculated with 100 $CCID_{50}$ of HIV-1 (HTLV-III) or HIV-2 (strain LAV-2).

The inhibition of MSV-transformation of murine C3H/3T3 fibroblasts was determined according to Balzarini et al., "Proc. Natl. Acad. Sci. USA" 86:332 (1989). The cell cultures were inoculated with 80 focus-forming units of MSV (prepared according to De Clercq and Merigan, "Proc. Soc. Exp. Biol. Med." 137:590 (1971).

The results are set forth in Tables 1–5. In these Tables, pyrrolidino, piperidino, morpholino, benzhydrylamino and furfurylamino shall be understood to mean, respectively, 6-(N-pyrrolo)purine, 6-(N-piperidino)purine, 6-(N-morpholino)purine, diphenylmethylamino and 6-((2-furyl)methylamino)purine. The antiviral activities are expressed as $EC_{50}$ in μg/ml; NA=not active; ND=not determined.

TABLE 1

Antiviral Activity of N6-Substituted 9-(R)-(2-Phosphonomethoxypropyl)purines (PMP-derivatives)

| 6-Substituent | HSV-1 (KOS) | HSV-2 (G) | HSV-1 TK⁻ B2006 | HSV-1 TK⁻ VMW1837 | CMV AD169 | CMV Davis | VZV TK⁺ OKA | VZV TK⁺ YS | VZV TK⁻ 07/1 | VZV TK⁻ YS/R | Vaccinia virus |
|---|---|---|---|---|---|---|---|---|---|---|---|
| | | | | N6-Substituted Adenines | | | | | | | |
| Amino | 150 | 70 | >200 | 300 | >100 | >100 | 35 | 57.6 | 8 | 28 | >200 |
| Ethylmethylamino | 0.7 | 2 | 2 | 0.7 | 0.13 | 0.28 | 0.007 | 0.011 | 0.005 | 0.005 | 20 |
| Allylamino | 2 | 2 | 7 | 2 | 0.9 | 0.8 | 0.016 | 0.032 | 0.011 | 0.015 | 70 |
| Cyclopropylamino | 2 | 2 | 2 | 0.7 | 0.6 | 0.35 | 0.009 | 0.013 | 0.004 | 0.007 | 20 |
| 2-Dimethylaminoethylamino | 2 | 7 | 7 | 0.7 | 1.1 | 1 | 0.038 | 0.039 | 0.022 | 0.03 | 70 |
| | | | | N6-Substituted 2,6-Diaminopurines | | | | | | | |
| Amino | 300 | 70 | — | 150 | NA | NA | NA | NA | NA | NA | 150 |
| Dimethylamino | 20 | >100 | >100 | 20 | >50 | >50 | 30 | 30 | 20 | 20 | >100 |
| 1-Butylamino | 70 | >100 | >100 | 70 | >50 | >50 | 30 | 50 | 30 | 35 | >100 |
| 2-Butylamino | 40 | >100 | >100 | 20 | >50 | >50 | 50 | 40 | 30 | 30 | 70 |
| 2-Methylpropylamino | NA | NA | NA | NA | >20 | >20 | >20 | >20 | >20 | >20 | NA |
| 1-Pentylamino | NA | NA | ND | NA | >50 | ND | >50 | ND | ND | ND | NA |
| Cyclopropylamino | 150 | >400 | 10 | 150 | >50 | >50 | 15 | 30 | 37 | 45 | 300 |
| Cyclopentylamino | 150 | >200 | >200 | >200 | >50 | >50 | >50 | >50 | >50 | >50 | 70 |
| Cyclohexylamino | 70 | >100 | 20 | 20 | >50 | >50 | 30 | 12 | 40 | 25 | >100 |
| Pyrrolidino | >200 | >200 | 400 | >200 | >50 | >50 | 5 | 40 | >50 | >50 | 150 |
| Piperidino | 70 | >100 | >100 | 70 | >50 | >50 | 33 | 40 | 50 | 50 | 70 |
| Morpholino | 70 | >100 | >100 | 70 | >50 | >50 | >50 | 20 | 40 | 50 | >100 |
| Benzylamino | 70 | >100 | 70 | 40 | >50 | >50 | 35 | 25 | 20 | 20 | 70 |
| Furfurylamino | NA | 300 | ND | 70 | >50 | ND | ND | ND | ND | ND | NA |
| 2-Dimethylaminoethylamino | 7 | 2 | 20 | 7 | 0.37 | 0.8 | 0.026 | 0.006 | 0.003 | 0.009 | 20 |

TABLE 2

Antiviral activity of N6-substituted 9-(2-phosphonomethoxyethyl)-2,6-diaminopurines

| 6-Substituent | HSV-1 (KOS) | HSV-2 (G) | HSV-1 TK⁻ B2006 | HSV-1 TK⁻ VMW1837 | CMV AD169 | CMV Davis | VZV TK⁺ OKA | VZV TK⁺ YS | VZV TK⁻ 07/1 | VZV TK⁻ YS/R | Vaccinia virus |
|---|---|---|---|---|---|---|---|---|---|---|---|
| Amino | 2 | 0.2 | — | 2 | 10 | 10 | 0.02 | 0.01 | 0.02 | 0.03 | 70 |
| Dimethylamino | 0.07 | 0.7 | 2 | 0.07 | 0.2 | 0.1 | 0.04 | 0.02 | 0.01 | 0.01 | 2 |
| Ethylmethylamino | 0.7 | 0.4 | 2 | 2 | 0.3 | 0.5 | 0.14 | 0.06 | 0.025 | 0.03 | 7 |
| Allylamino | 0.7 | 0.7 | 4 | 0.7 | 0.2 | 0.3 | 0.17 | 0.11 | 0.1 | 0.06 | 7 |
| 1-Butylamino | 2 | 40 | 2 | 2 | 6 | 1.5 | 1.1 | 1.3 | 2 | 1.3 | 7 |
| 2-Butylamino | 7 | 70 | 7 | 7 | 9 | 3 | 1.2 | 3 | 2 | 4.3 | 10 |
| 2-Methylpropylamino | 2 | 7 | 7 | 7 | 0.8 | 1.2 | 0.16 | 0.17 | 0.32 | 0.15 | 20 |
| Cyclopropylamino | 0.2 | 0.7 | 0.2 | 0.2 | 0.2 | 0.12 | 0.009 | 0.03 | 0.08 | 0.05 | 0.7 |
| Cyclopentylamino | 2 | 20 | 2 | 10 | 5 | 2 | 1 | 2.35 | 3 | 1.35 | 20 |
| Cyclohexylamino | 2 | 7 | 2 | 0.7 | 1 | 2.5 | 1 | 1.4 | 0.2 | 0.2 | 20 |
| Pyrrolidino | 2 | 10 | 0.7 | 7 | 2 | 0.9 | 0.2 | 0.38 | 0.85 | 1 | 20 |
| Piperidino | 0.7 | 7 | 10 | 0.7 | 0.9 | 1 | 1.4 | 0.9 | 0.2 | 0.2 | 4 |
| Morpholino | 7 | 20 | 10 | 7 | 10 | 10 | 1.5 | 8 | 4 | 6 | 70 |
| Benzylamino | 2 | 40 | 70 | 2 | 5 | 10 | 4 | 2 | 3 | >50 | 20 |
| Phenethylamino | 20 | 20 | NA | 20 | 10 | 15 | 7 | 10 | 7 | 3.3 | 70 |
| Phenylamino | 70 | 70 | 70 | 70 | 7 | 7 | 1.2 | 3 | 1 | 2 | 300 |
| Benzhydrylamino | 2 | 7 | 20 | 2 | 1.2 | 1 | 0.06 | 0.05 | 0.029 | 0.032 | 20 |
| α-Naphtylamino | 150 | 150 | NA | NA | >50 | >50 | 20 | 50 | 25 | ND | 300 |
| 2-Dimethylaminoethyl-amino | 7 | 2 | 10 | 7 | 0.2 | 0.3 | 0.03 | 0.026 | 0.02 | 0.022 | 20 |
| 3-Dimethylaminopropyl-amino | 7 | 7 | 20 | 20 | 1.3 | 1 | 0.1 | 0.068 | 0.028 | 0.03 | 70 |

TABLE 3

Antiviral activity of N6-substituted 9-(2-phosphonomethoxyethyl)adenines

| 6-Substituent | HSV-1 (KOS) | HSV-2 (G) | HSV-1 TK⁻ B2006 | HSV-1 TK⁻ VMW1837 | CMV AD169 | CMV Davis | VZV TK⁺ OKA | VZV TK⁺ YS | VZV TK⁻ 07/1 | VZV TK⁻ YS/R | Vaccinia virus |
|---|---|---|---|---|---|---|---|---|---|---|---|
| Amino | 20 | 2 | — | 7 | 70 | — | 6 | 10 | 6 | 10 | 100 |
| Dimethylamino | 7 | 20 | 70 | 7 | 9 | 9 | 1.6 | 3.2 | 0.9 | 4 | 300 |
| Diethylamino | 2 | 2 | 7 | 0.7 | 0.9 | 0.8 | 0.016 | 0.029 | 0.013 | 0.007 | 20 |
| 2-Methylpropylamino | 20 | 70 | 20 | 20 | 25 | 13 | 0.65 | 0.9 | 0.27 | 0.2 | NA |
| Allylamino | 2 | 7 | 7 | 2 | 0.5 | 0.5 | 0.032 | 0.02 | 0.016 | 0.01 | 20 |
| Cyclopropylamino | 40 | 150 | ND | 70 | 25 | 23 | 3.5 | 5 | 1.6 | 4 | NA |
| Cyclohexylamino | 20 | 20 | 70 | 20 | 11 | 9 | 1.4 | 1.5 | 0.4 | 0.8 | >400 |
| Pyrrolidino | 20 | 70 | ND | 20 | 12 | 12 | 0.29 | 0.25 | 0.2 | 0.24 | NA |
| Piperidino | 20 | 70 | ND | 20 | 15 | 11 | 0.3 | 0.5 | 0.2 | 0.2 | NA |
| 2-Dimethylaminoethyl-amino | 20 | 70 | 70 | 20 | 13 | 13 | 1.5 | 5 | 2 | 0.2 | >200 |

TABLE 4

Anti-retroviral activity of 9-(2-Phosphonomethoxyethyl)purines (PME-derivatives)

| | | HIV-1 | | HIV-2 | |
|---|---|---|---|---|---|
| 6-Substituent | MSV | MT-4 | CEM | MT-4 | CEM |
| *N6-Substituted Adenine Derivatives* | | | | | |
| Amino | 1.14 ± 0.04 | >4 | | | |
| Dimethylamino | | | >100 | | 85 ± 21.2 |
| Diethylamino | | | >4 | | >4 |
| Allylamino | | | 8 ± 5.7 | | 5 ± 1.4 |
| Cyclohexyiamino | | | >100 | | >100 |
| 2-Dimethylaminoethylamino | | | >100 | | 75 ± 35.4 |
| *N6-Substituted 2,6-Diaminopurine Derivatives* | | | | | |
| Amino | 0.60 ± 0.33 | 2.67 ± 1.53 | ND | ND | ND |
| Dimethylamino | 0.24 ± 0.07 | 0.4 ± 0.01 | 0.7 ± 0.1 | 0.4 ± 0.05 | 0.8 |
| Ethylmethylamino | 0.26 ± 0.17 | 0.19 ± 0.16 | 0.55 ± 0.35 | 0.11 ± 0.04 | 0.2 ± 0 |
| Allylamino | 0.14 ± 0.11 | >100 | >0.032 | | >0.032 |
| 1-Butylamino | 4.08 ± 2.12 | 2.15 ± 2.13 | 2 | 2.3 ± 2.3 | 1.4 ± 0.85 |
| 2-Butylamino | 3.2 | 1.97 ± 0.08 | 3 | 2.0 ± 0.2 | 3 |
| 2-Methylpropylamino | NA | >0.16 | 0.5 | >0.16 | 0.3 |
| Cyclopropylamino | 0.11 | 0.11 ± 0.05 | 0.16 | 0.1 ± 0.03 | 0.16 |
| Cyclopentylamino | 2.62 ± 1.77 | >0.8 | 2 | >0.8 | 1.75 ± 0.35 |
| Cyclohexylamino | 0.26 ± 0.6 | 5.7 ± 4 | 20 | 4.8 ± 4 | >20 |
| Pyrrolidino | 0.75 | 1.88 ± 0.25 | 2.17 | 2 ± 0.3 | 1.65 ± 1.2 |
| Piperidino | 0.75 ± 0.6 | 3.0 ± 1.3 | >4 | 3.0 ± 1.3 | >4 |
| Morpholino | 3.4 ± 2.3 | 15 ± 0.2 | >20 | 16 ± 0.3 | >20 |
| Benzylamino | 1.5 ± 0.94 | 50 ± 12 | >20 | 49 ± 21 | >20 |
| Phenethylamino | 21.8 ± 7.5 | 9.9 ± 0.9 | 16 ± 5.7 | 11.9 ± 2.8 | 12.5 ± 3.5 |
| Phenylamino | 4.68 ± 0.79 | 56.3 ± 14.1 | 63.3 ± 32.1 | 35.1 ± 22.3 | 35 ± 7 |
| α-Napthylamino | 47.6 ± 33.1 | 90.0 ± 17.3 | >100 | 68.5 ± 2.5 | 80 ± 28 |
| 2-Dimethylaminoethylamino | 0.20 ± 0.02 | 3.25 ± 0.75 | 5.5 ± 2.1 | 2.39 ± 0.77 | 2 ± 0.7 |
| 3-Dimethylaminopropylamino | 0.40 ± 0.07 | 6.12 ± 3.73 | 13.0 ± 6.6 | 7.03 ± 4.9 | 4 ± 0 |

TABLE 5

Anti-retroviral Activity of N6-Substituted 9-(R)-(2-Phosphonomethoxyethyl) Purines (PMP-derivatives)

| | | HIV-1 | | HIV-2 | |
|---|---|---|---|---|---|
| 6-Substituent | MSV | MT-4 | CEM | MT-4 | CEM |
| *N6-Substituted Adenine Derivatives* | | | | | |
| Amino | 0.95 ± 0.23 | 1.91 ± 0.41 | | 1.69 ± 0.35 | |
| Ethylmethylamino | | | 5.5 ± 2.1 | | 4 |
| Allylamino | | | 12 ± 2.8 | | 12 |
| Cyclopropylamino | | | 10 ± 0 | | 9.5 ± 3.5 |
| 2-Dimethylaminoethylamino | | | >4 | | >4 |

TABLE 5-continued

Anti-retroviral Activity of N6-Substituted
9-(R)-(2-Phosphonomethoxyethyl) Purines (PMP-derivatives)

| 6-Substituent | MSV | HIV-1 MT-4 | HIV-1 CEM | HIV-2 MT-4 | HIV-2 CEM |
|---|---|---|---|---|---|
| N6-Substituted 2,6-Diaminopurine Derivatives | | | | | |
| Amino | 0.073 ± 0.02 | 0.293 ± 0 | — | 0.236 ± 0.03 | — |
| Dimethylamino | 3.25 ± 1.44 | 2.3 ± 0.2 | 10 | 4.2 ± 2.8 | 9 ± 1.4 |
| 1-Butylamino | 3.27 ± 1.3 | 13.1 ± 4.3 | 10 | 9.8 ± 4.9 | 10 |
| 2-Butylamino | 3.5 ± 0.3 | 30 ± 19 | >100 | 25 ± 15 | >100 |
| 2-Methylpropylamino | 22.7 ± 12.7 | 57.4 ± 17.8 | 5.5 ± 2.1 | 55.9 ± 14 | 5.5 ± 2.1 |
| 1-Pentylamino | 5.14 | 37.4 ± 13 | 20 | 37.7 ± 5.8 | 15 ± 7.1 |
| Cyclopropylamino | 1.09 ± 0.24 | 4.15 ± 3 | 2 | 3.2 ± 1.6 | 2.5 ± 0.7 |
| Cyclopentylamino | 3.78 ± 0.08 | 3.4 ± 0.4 | 4.5 ± 3.5 | 5.8 ± 2.3 | 8.5 ± 2.1 |
| Cyclohexylamino | 1.4 ± 1.2 | 8.0 ± 2 | 20 ± 17 | 7 ± 2.6 | 13 ± 6 |
| Pyrrolidino | 5.09 ± 1.65 | 36.9 ± 5.7 | 50 ± 14 | 47.7 ± 7 | 50 |
| Piperidino | 12.6 ± 10 | >100 | >100 | >100 | >100 |
| Morpholino | 6.1 ± 2.3 | >100 | >100 | >100 | >100 |
| Benzylamino | 0.3 ± 0.11 | 10.3 ± 1.4 | 11 ± 6 | 8 ± 2.9 | 12.5 ± 3.5 |
| Furfurylamino | 2 ± 1 | 10 | 7.0 ± 4.2 | 7.74 ± 1.33 | 6.0 ± 5.7 |
| 2-Dimethylaminoethylamino | 0.77 ± 0.34 | 6.23 ± 4.48 | 7 | 4.65 ± 2.59 | 3.3 ± 1.1 |

All citations are hereby expressly incorporated by reference. The following examples are illustrative and do not limit the scope of this invention.

The claims shall be construed to exclude any subject matter that, at the date of the invention demonstrable under 35 USC 104, would not have been patentable under applicable statutory and judicial authority. In particular, the claims are to be construed as excluding any subject matter in any prior art citation herein that would have been obvious under 35 USC 103 or is anticipated under 35 USC 102.

We claim:

1. A method comprising treating a subject infected by a DNA virus with a therapeutically acceptable dose of a compound having structure (1)

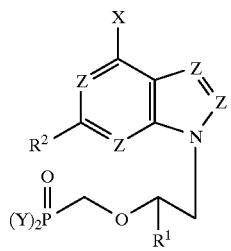

(1)

wherein

Y independently is, OH, —$OR^3$, —$OCH(R^{16})OC(O)R^3$, a monophosphate, a diphosphate, an amino acid amidate, a polypeptide amidate, —$NHR^3$, or —$N(R^3)_2$;

$R^3$ independently is unsubstituted alkyl, aryl, alkenyl, alkynyl, alkaryl, alkynylaryl or alkenylaryl; alkyl, aryl, alkenyl, alkynyl, alkaryl, alkynylaryl or alkenylaryl wherein H is substituted by halo, carboxy, hydroxyl, cyano, nitro, N-morpholino, or amino; or alkyl, alkenyl, alkynyl, alkaryl, alkynylaryl or alkenylaryl in which a —$CH_2$— moiety has been substituted by NH, S, or O;

$R^2$ is $NH_2$ or H;

$R^1$ is $CH_3$, C≡CH, CH=$CH_2$, $CH_2F$ or azidomethyl;

$R^{16}$ is H or $R^3$; and

X is —$N(R^{10})_2$ wherein $R^{10}$ independently is

H;

$C_2$–$C_{15}$ alkyl, $C_3$–$C_{15}$ alkenyl, $C_6$–$C_{15}$ arylalkenyl, $C_3$–$C_{15}$ alkynyl, $C_7$–$C_{15}$ arylalkynyl, $C_1$–$C_6$-alkylamino-$C_1$–$C_6$ alkyl, $C_5$–$C_{15}$ aralkyl, $C_6$–$C_{15}$ heteroalkyl or $C_3$–$C_6$ heterocycloalkyl wherein methylene in an alkyl moiety not adjacent to NH has been replaced by —O—;

$C_1$–$C_{15}$ alkyl, $C_2$–$C_{15}$ alkenyl, $C_6$–$C_{15}$ arylalkenyl, $C_6$–$C_{15}$ arylalkynyl, $C_2$–$C_{15}$ alkynyl, $C_1$–$C_6$-alkylamino-$C_1$–$C_6$ alkyl, $C_5$–$C_{15}$ aralkyl, $C_6$–$C_{15}$ heteroaralkyl, $C_4$–$C_6$ aryl, $C_2$–$C_6$ heterocycloalkyl;

optionally both $R^{10}$ are joined together to form a saturated or unsaturated $C_2$–$C_5$ heterocycle containing one or two N heteroatoms and optionally an additional O or S heteroatom, or one of the foregoing $R^{10}$ groups in which 1 to 3 H are substituted with halo, CN or $N_3$, but either one or two $R^{10}$ groups are not H; and Z is N or CH, provided that no more than one Z varies from purine;

and the therapeutically acceptable salts thereof.

2. The method of claim 1 wherein $R^1$ is $CH_3$, Y is OH or $OR^3$, $R^2$ is H and X is —$N(CH_3)(CH_2CH_3)$, —$N(CH_2CH_3)_2$, —$NHCH_2CH$=$CH_2$, —$NH(CH_2)_2CH$=$CH_2$, —NH(cyclopropyl), —$NH(CH_2)_2N(CH_3)_2$, —$NH(CH_2)_3N(CH_3)_2$, $NH(CH_2)_2N(CH_3)(CH_2CH_3)$, $NH(CH_2)_3N(CH_3)(CH_2CH_3)$, —$NH(CH_2)_2NH(cyclopropyl)$, —$NH(CH_2)_3NH(cyclopropyl)$, —$NH(CH_2)_2NHCH_2(cyclopropyl)$, —$NH(CH_2)_3NHCH_2(cyclopropyl)$, —$NH(CH_2)_2NHCH_2CH$=$CH_2$, —$NH(CH_2)_3NHCH_2CH$=$CH_2$, —$NHCH_2C$≡$CH$ or —$NHCH_2CH$=$CH(Phe)$.

3. The method of claim 1 wherein one $R^{10}$ group is not H.

4. The method of claim 1 wherein both $R^{10}$ groups are not H.

5. The method of claim 1 wherein one $R^{10}$ is $C_3$–$C_4$ cycloalkyl.

6. The method of claim 1 wherein one $R^{10}$ is $C_1$–$C_6$-alkylamino-$C_1$–$C_6$-alkyl.

7. The method of claim 1 wherein one $R^{10}$ is $C_2$–$C_{15}$ alkenyl or $C_3$–$C_{15}$ alkynyl.

8. The method of claim 1 wherein one $R^{10}$ is —$(CH_2)_2N(CH_3)(CH_2CH_3)$, $(CH_2)_2N(CH_3)_2$, $(CH_2)_3N(CH_3)_2$

—CH$_2$NHCH$_2$CH$_2$OCH$_2$N(CH$_3$)$_2$, —CH$_2$NHCH$_2$OCH$_2$N(CH$_3$)$_2$,

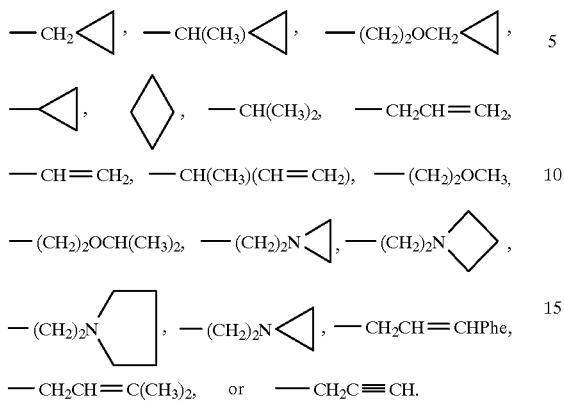

9. The method of claim 1 wherein R$^1$ is CH$_3$ in the (R) configuration.

10. The method of claim 1 wherein R$^2$ is H.

11. The method of claim 1 wherein R$^1$ is CH$_3$.

12. The method of claim 1 wherein the compound is 9-(R)-(2-phosphonomethoxypropyl)-6-ethylmethylaminoadenine, 9-(R)-(2-phosphonomethoxypropyl)-6-allylaminoadenine, 9-(R)-(2-phosphonomethoxypropyl)-6-cyclopropylaminoadenine, 9-(R)-(2-phosphonomethoxypropyl)-6-(2-dimethylaminoethyl)aminoadenine or 9-(R)-(2-phosphonomethoxypropyl)-2-amino-6-(2-dimethylaminoethyl)aminoadenine.

13. The method of claim 11 wherein the virus is VZV.

14. The method of claim 1 wherein the DNA virus is a herpesvirus.

15. A compound having structure (2)

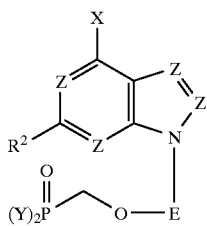

wherein
Y independently is, OH, —OR$^3$, —OCH(R$^{16}$)OC(O)R$^3$, a monophosphate, a diphosphate, an amino acid amidate, a polypeptide amidate, —NHR$^3$, or —N(R$^3$)$_2$;
X is —N(R$^{10}$)$_2$;
Z is N or CH, provided that no more than one Z varies from purine;
R$^3$ independently is unsubstituted alkyl, aryl, alkenyl, alkynyl, alkaryl, alkynylaryl or alkenylaryl; alkyl, aryl, alkenyl, alkynyl, alkaryl, alkynylaryl or alkenylaryl wherein H is substituted by halo, carboxy, hydroxyl, cyano, nitro, N-morpholino, or amino; or alkyl, alkenyl, alkynyl, alkaryl, alkynylaryl or alkenylaryl in which a —CH$_2$— moiety has been substituted by NH, S, or O;
R$^2$ is NH$_2$ or H;
E is —(CH$_2$)$_2$—, —CH(CH$_3$)CH$_2$—, —CH(CH$_2$F)CH$_2$—, —CH(CH$_2$OH)CH$_2$—, —CH(CH=CH$_2$)CH$_2$—, —CH(C≡CH)CH$_2$—, —CH(CH$_2$N$_3$)CH$_2$—,

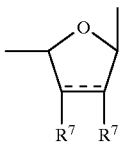

—CH(R$^6$)OCH(R$^{6'}$)—, —CH(R$^9$)CH$_2$O— or —CH(R$^8$)O—, wherein the right hand bond is linked to the 9 position of the purine, monoazapurine or monodeazapurine heterocycle;
the broken line represents an optional bond;
R$^6$ and R$^{6'}$ are independently H, C$_1$–C$_6$ alkyl, C$_1$–C$_6$ hydroxyalkyl, or C$_2$–C$_7$ alkanoyl;
R$^7$ independently are H, C$_1$–C$_6$ alkyl, or are taken together to form —O— or —CH$_2$;
R$^8$ is H, C$_1$–C$_6$ alkyl, C$_1$–C$_6$ hydroxyalkyl or C$_1$–C$_6$ haloalkyl;
R$^9$ is H, hydroxymethyl or acyloxymethyl; and
R$^{10}$ independently is
H;
C$_2$–C$_{15}$ alkyl, C$_3$–C$_{15}$ alkenyl, C$_6$–C$_{15}$ arylalkenyl, C$_3$–C$_{15}$ alkynyl, C$_7$–C$_{15}$ arylalkynyl, C$_1$–C$_6$-alkylamino-C$_1$–C$_6$ alkyl, C$_5$–C$_{15}$ aralkyl, C$_6$–C$_{15}$ heteroalkyl or C$_3$–C$_6$ heterocycloalkyl wherein methylene in an alkyl moiety not adjacent to NH has been replaced by —O—;
C$_2$–C$_{15}$ alkenyl, C$_6$–C$_{15}$ arylalkenyl, C$_6$–C$_{15}$ arylalkynyl, C$_2$–C$_{15}$ alkynyl, C$_1$–C$_6$-alkylamino-C$_1$–C$_6$ alkyl, C$_6$–C$_{15}$ heteroaralkyl, or C$_2$–C$_6$ heterocycloalkyl;
optionally both R$^{10}$ are joined together to form a saturated or unsaturated C$_2$–C$_5$ heterocycle containing one or two N heteroatoms and optionally an additional O or S heteroatom,
or one of the foregoing R$^{10}$ groups in which 1 to 3 H are substituted with halo, CN or N$_3$
but either one or two R$^{10}$ groups are not H; and
R$^{16}$ is H or R$^3$; and
the therapeutically acceptable salts thereof.

16. The compound of claim 15 wherein at least one Y is OR$^3$ and R$^3$ is aryl, ortho-alkoxyaryl, or —C$_6$H$_4$C(O)OC$_2$H$_5$.

17. The compound of claim 15 wherein R$^3$ is ortho-C$_1$–C$_5$-alkoxyphenyl.

18. The compound of claim 15 wherein Y is —OCH$_2$OC(O)R$^3$.

19. The compound of claim 15 wherein R$^3$ is —C(CH$_3$)$_3$.

20. The compound of claim 15 which has the (S) configuration at an E chiral carbon atom.

21. The compound of claim 15 which has the (R) configuration.

22. The compound of claim 15 wherein one R$^{10}$ group is not H.

23. The compound of claim 15 wherein both R$^{10}$ groups are not H.

24. A method for treatment of viral infections comprising administering to a subject an antivirally effective amount of a compound having structure (2)

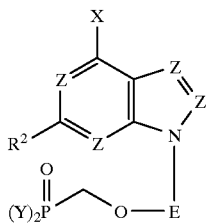

wherein

Y independently is, OH, —OR$^3$, —OCH(R$^{16}$)OC(O)R$^3$, a monophosphate, a diphosphate, an amino acid amidate, a polypeptide amidate, —NHR$^3$, or —N(R$^3$)$_2$;

X is —N(R$^{10}$)$_2$;

Z is N or CH, provided that no more than one Z varies from purine;

R$^3$ independently is unsubstituted alkyl, aryl, alkenyl, alkynyl, alkaryl, alkynylaryl or alkenylaryl; alkyl, aryl, alkenyl, alkynyl, alkaryl, alkynylaryl or alkenylaryl wherein H is substituted by halo, carboxy, hydroxyl, cyano, nitro, N-morpholino, or amino; or alkyl, alkenyl, alkynyl, alkaryl, alkynylaryl or alkenylaryl in which a —CH$_2$— moiety has been substituted by NH, S, or O;

R$^2$ is NH$_2$ or H;

E is —(CH$_2$)$_2$—, —CH(CH$_3$)CH$_2$—, —CH(CH$_2$F) CH$_2$—, —CH(CH$_2$OH)CH$_2$—, —CH(CH=CH$_2$) CH$_2$—, —CH(C≡CH)CH$_2$—, —CH(CH$_2$N$_3$)CH$_2$—,

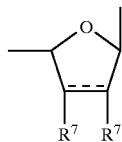

—CH(R$^6$)OCH(R$^{6'}$)—, —CH(R$^9$)CH$_2$O— or —CH(R$^8$)O—, wherein the right hand bond is linked to the 9 position of the purine, monoazapurine or monodeazapurine heterocycle;

the broken line represents an optional bond;

R$^6$ and R$^{6'}$ are independently H, C$_1$–C$_6$ alkyl, C$_1$–C$_6$ hydroxyalkyl, or C$_2$–C$_7$ alkanoyl;

R$^7$ independently are H, C$_1$–C$_6$ alkyl, or are taken together to form —O— or —CH$_2$;

R$^8$ is H, C$_1$–C$_6$ alkyl, C$_1$–C$_6$ hydroxyalkyl or C$_1$–C$_6$ haloalkyl;

R$^9$ is H, hydroxymethyl or acyloxymethyl; and

R$^{10}$ independently is

H;

C$_2$–C$_{15}$ alkyl, C$_3$–C$_{15}$ alkenyl, C$_6$–C$_{15}$ arylalkenyl, C$_3$–C$_{15}$ alkynyl, C$_7$–C$_{15}$ arylalkynyl, C$_1$–C$_6$-alkylamino-C$_1$–C$_6$ alkyl, C$_5$–C$_{15}$ aralkyl, C$_6$–C$_{15}$ heteroalkyl or C$_3$–C$_6$ heterocycloalkyl wherein methylene in an alkyl moiety not adjacent to NH has been replaced by —O—;

C$_2$–C$_{15}$ alkenyl, C$_6$–C$_{15}$ arylalkenyl, C$_6$–C$_{15}$ arylalkynyl, C$_2$–C$_{15}$ alkynyl, C$_1$–C$_6$-alkylamino-C$_1$–C$_6$ alkyl, C$_6$–C$_{15}$ heteroaralkyl, or C$_2$–C$_6$ heterocycloalkyl;

optionally both R$^{10}$ are joined together to form a saturated or unsaturated C$_2$–C$_5$ heterocycle containing one or two N heteroatoms and optionally an additional O or S heteroatom, or one of the foregoing R$^{10}$ groups in which 1 to 3 H are substituted with halo, CN or N$_3$ but either one or two R$^{10}$ groups are not H; and R$^{16}$ is H or R$^3$; and the therapeutically acceptable salts thereof.

25. The method of claim 24 wherein the viral infection is HSV-1, HSV-2, CMV, VZV, vaccinia virus, or HHV-6.

26. The method of claim 24 wherein the compound is administered orally, topically, intravitreally or intrathecally.

27. The method of claim 26 wherein one R$^{10}$ group is not H.

28. The method of claim 26 wherein both R$^{10}$ groups are not H.

29. A compound having structure (1)

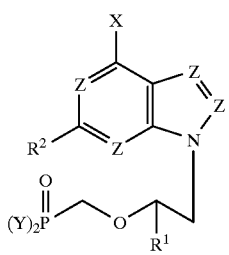

wherein

Y independently is, OH, —OR$^3$, —OCH(R$^{16}$)OC(O)R$^3$, a monophosphate, a diphosphate, an amino acid amidate, a polypeptide amidate, —NHR$^3$, or —N(R$^3$)$_2$;

R$^3$ independently is unsubstituted alkyl, aryl, alkenyl, alkynyl, alkaryl, alkynylaryl or alkenylaryl; alkyl, aryl, alkenyl, alkynyl, alkaryl, alkynylaryl or alkenylaryl wherein H is substituted by halo, carboxy, hydroxyl, cyano, nitro, N-morpholino, or amino; or alkyl, alkenyl, alkynyl, alkaryl, alkynylaryl or alkenylaryl in which a —CH$_2$— moiety has been substituted by NH, S, or O;

R$^2$ is NH$_2$;

R$^1$ is CH$_3$, C≡CH, CH=CH$_2$, CH$_2$F or azidomethyl;

R$^{16}$ is H or R$^3$; and

X is -N(R$^{10}$)$_2$ wherein

R$^{10}$ independently is

H;

C$_3$–C$_4$ cycloalkyl-substituted C$_1$–C$_2$ alkyl, C$_2$–C$_{15}$ alkenyl, C$_6$–C$_{15}$ arylalkenyl, C$_6$–C$_{15}$ arylalkynyl, C$_2$–C$_{15}$ alkynyl, C$_1$–C$_6$-alkylamino-C$_1$–C$_6$ alkyl, C$_6$–C$_{15}$ heteroaralkyl, C$_4$–C$_6$ aryl, C$_2$–C$_6$ heterocycloalkyl, —CH(Phe)$_2$, or C$_3$–C$_4$ cycloalkyl which C$_3$–C$_4$ cycloalkyl is mono-, di- or tri-substituted with C$_1$–C$_3$ alkyl;

C$_2$–C$_{15}$ branched or normal alkyl, C$_3$–C$_{15}$ alkenyl, C$_6$–C$_{15}$ arylalkenyl, C$_3$–C$_{15}$ alkynyl, C$_7$–C$_{15}$ arylalkynyl, C$_1$–C$_6$-alkylamino-C$_1$–C$_6$ alkyl, C$_5$–C$_{15}$ aralkyl, C$_6$–C$_{15}$ heteroalkyl or C$_3$–C$_6$ heterocycloalkyl wherein methylene in an alkyl moiety not adjacent to NH has been replaced by —O—;

optionally both R$^{10}$ are joined together to form a saturated or unsaturated C$_2$–C$_5$ heterocycle containing one or two N heteroatoms and optionally an additional O or S heteroatom, or one of the foregoing $R^{10}$ groups in which 1 to 3 H are substituted with halo, CN or $N_3$
but either one or two $R^{10}$ groups are not H; and Z is N or CH, provided that no more than one Z varies from purine; and the therapeutically acceptable salts thereof.

30. A compound having structure (1)

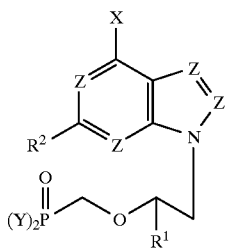
(1)

wherein
Y is OH;
$R^2$ is H;
$R^1$ is $CH_3$;
X is $C_1$–$C_{15}$ alkylamino; and
Z is N or CH, provided that no more than one Z varies from purine;
and the therapeutically acceptable salts thereof.

31. A compound having structure (1)

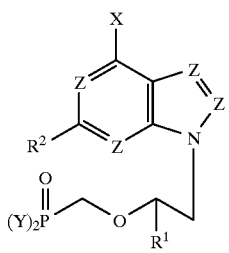
(1)

wherein
Y is OH;
$R^2$ is H;
$R^1$ is $CH_3$;
X is ethylmethylamino, allylamino, cyclopropylamino or 2-dimethylaminoethylamino; and
Z is N or CH, provided that no more than one Z varies from purine;
and the therapeutically acceptable salts thereof.

32. A compound having structure

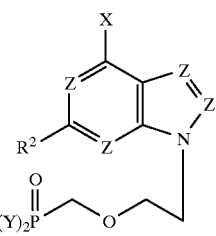

wherein
Y independently is, OH, —$OR^3$, —$OCH(R^{16})OC(O)R^3$, a monophosphate, a diphosphate, an amino acid amidate, a polypeptide amidate, —$NHR^3$, or —$N(R^3)_2$;
$R^3$ independently is unsubstituted alkyl, aryl, alkenyl, alkynyl, alkaryl, alkynylaryl or alkenylaryl; alkyl, aryl, alkenyl, alkynyl, alkaryl, alkynylaryl or alkenylaryl wherein H is substituted by halo, carboxy, hydroxyl, cyano, nitro, N-morpholino, or amino; or alkyl, alkenyl, alkynyl, alkaryl, alkynylaryl or alkenylaryl in which a —$CH_2$— moiety has been substituted by NH, S, or O;
$R^2$ is $NH_2$ or H;
$R^{16}$ is H or $R^3$; and
X is —$N(R^{10})_2$ wherein
$R^{10}$ independently is
  H;
  $C_2$–$C_{15}$ alkyl, $C_3$–$C_{15}$ alkenyl, $C_6$–$C_{15}$ arylalkenyl, $C_3$–$C_{15}$ alkynyl, $C_7$–$C_{15}$ arylalkynyl, $C_1$–$C_6$-alkylamino-$C_1$–$C_6$ alkyl, $C_5$–$C_{15}$ aralkyl, $C_6$–$C_{15}$ heteroalkyl or $C_3$–$C_6$ heterocycloalkyl wherein methylene in an alkyl moiety not adjacent to NH has been replaced by —O—;
  $C_1$–$C_{15}$ alkyl, $C_2$–$C_{15}$ alkenyl, $C_6$–$C_{15}$ arylalkenyl, $C_6$–$C_{15}$ arylalkynyl, $C_2$–$C_{15}$ alkynyl, $C_1$–$C_6$-alkylamino-$C_1$–$C_6$ alkyl, $C_5$–$C_{15}$ aralkyl, $C_6$–$C_{15}$ heteroaralkyl, $C_4$–$C_6$ aryl, $C_2$–$C_6$ heterocycloalkyl;
  optionally both $R^{10}$ are joined together to form a saturated or unsaturated $C_2$–$C_5$ heterocycle containing one or two N heteroatoms and optionally an additional O or S heteroatom,
  or one of the foregoing $R^{10}$ groups in which 1 to 3 H are substituted with halo, CN or $N_3$,
  but either one or two $R^{10}$ groups are not H; and
Z is N or CH, provided that no more than one Z varies from purine;
and the therapeutically acceptable salts thereof.

33. 9-(2-phosphonomethoxypropyl)-2-amino, 6-(2-dimethylamino-ethylamino)purine.

* * * * *